US006498013B1

(12) United States Patent
Velculescu et al.

(10) Patent No.: US 6,498,013 B1
(45) Date of Patent: Dec. 24, 2002

(54) SERIAL ANALYSIS OF TRANSCRIPT EXPRESSION USING MMEI AND LONG TAGS

(75) Inventors: Victor E. Velculescu, Baltimore, MD (US); Andrew Sparks, Baltimore, MD (US); Kenneth W. Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/916,228

(22) Filed: Jul. 27, 2001

Related U.S. Application Data

(60) Provisional application No. 60/221,556, filed on Jul. 28, 2000, and provisional application No. 60/233,431, filed on Sep. 18, 2000.

(51) Int. Cl.[7] .............................. C12Q 1/68; C12P 19/34
(52) U.S. Cl. ........................... 435/6; 435/91.1; 435/91.2
(58) Field of Search ........................... 435/6, 91.2, 91.1

(56) References Cited

U.S. PATENT DOCUMENTS

| | | | | |
|---|---|---|---|---|
| 5,695,937 A | * | 12/1997 | Kinzler et al. | 435/6 |
| 5,866,330 A | * | 2/1999 | Kinzler et al. | 435/6 |
| 6,383,743 B1 | * | 5/2002 | Kinzler et al. | |
| 2002/0065609 A1 | * | 5/2002 | Ashby | |

FOREIGN PATENT DOCUMENTS

| | | | | |
|---|---|---|---|---|
| GB | | 1024201 A | * 1/1999 | 435/6 |

OTHER PUBLICATIONS

Tucholski, J. et al., "M*me*I, a class–IIS restriction endonuclease: purification and characterization*", *Gene*, 157, (1995) pp. 87–92.

Szybalski, W., "Universal restriction endonucleases: designing novel cleavage specificities by combining ada oligodeoxynucleotide and enzyme moieties", *Gene*, 40, (1985), pp. 169–173.

Gunnersen, j. et al., Growth and Migration Markets of Rat C6 Glioma Cells Identified by Serial Analysis of Gene Expression, *GLIA*, 32, (2000), pp. 146–154.

Yamashita, T., "Serial Analysis of Gene Expression in Chronic Hepatitis C and Hepatocellular Carcinoma", *Biochemical and Biophysical Research Communications*, 282 (2001), pp. 647–654.

Jansen, B. et al., "Serial Analysis of Gene Expression in Differentiated Cultures of Human Epidermal Keratinocytes", *The Journal of Investigative Dermatology*, 116, No. 1, (2001), pp. 12–22.

Parle–McDermott, A.. et al., "Serial analysis of gene expression identifies putative metastasis–associated transcripts in colon tumour cell lines", *British Journal of Cancer*, 83, (2000), pp. 725–728.

Van Limpt, V. et al., "SAGE Analysis of Neuroblastoma Reveals a High Expression of the Human Homologue of the *Drosophila Delta* Gene", *Medical and Pediatric Oncology*, 35, (2000), pp. 554–558.

Virlon, B. et al., "Serial microanalysis of renal transcriptomes", *PNAS*, 96, No. 26, (1999), pp. 15286–15291.

Waghray, A.. et al., "Identification of Differentially Expressed Genes by Serial Analysis of Gene Expression in Human Prostate Cancer", *Cancer Research*, 61, No. 10, pp. 4283–4286.

Angelastro, J. et al., "Identification of diverse nerve growth factor–regulated genes by serial analysis of gene expression (SAGE) profiling", *PNAS*, 97, No. 19, (2000), pp. 10424–10429.

Wang, S. et al., "A strategy for genome–wide gene analysis: Integrated procedure for gene identification", *PNAS*, 95, (1998), pp. 11909–11914.

Lee, S. et al., "The pattern of gene expression in human $CD15^+$ myeloid progenitor cells", *PNAS*, 98, No. 6, (2001), pp. 3340–3345.

Hashimoto, Shin-ichi et al., "Identification of genes specifically expressed in human activated and mature dendritic cells through serial analysis of gene expression", *Blood*, 96, No. 6, (2000), pp. 2206–2214.

Sun, Y. et al., "Serial analysis of gene expression in the frontal cortex of patients with bipolar disorder", *British Journal of Psychiatry*, 178(41), (2001), pp. s137–s141.

Takano, T. et al., "Gene expression profiles in thyroid carcinomas", *Britsh Journal of Cancer*, 83(11), (2002), pp. 1495–1502.

Boon, K. et al., "N–myc enhances the expression of a large set of genes functioning in ribosome biogenesis and protein synthesis", *The EMBO Journal*, 20, No. 6, (2001), pp. 1383–1393.

Matsumura, H. et al., Transcript profiling in rice (*Oryza sativa L.*) seedlings using serial analysis of gene expression (SAGE), *The Plant Journal*, 20(6), (1999), pp. 719–725.

Ryo, A.. et al., "Serial analysis of gene expression in HIV–1 infected T cell lines", *FEBS Letters*, 462, (1999), pp. 182–186.

(List continued on next page.)

*Primary Examiner*—Kenneth R. Horlick
(74) *Attorney, Agent, or Firm*—Banner & Witcoff, Ltd.

(57) ABSTRACT

Serial analysis of gene expression, SAGE, a method for the rapid quantitative and qualitative analysis of transcripts, has been improved to provide more genetic information about each analyzed transcript by use of MmeI restriction endonuclease. In SAGE, defined sequence tags corresponding to expressed genes are isolated and analyzed. Sequencing of over 1,000 defined tags in a short period of time (e.g., hours) reveals a gene expression pattern characteristic of the function of a cell or tissue. Moreover, SAGE is useful as a gene discovery tool for the identification and isolation of novel sequence tags corresponding to novel transcripts and genes.

30 Claims, 8 Drawing Sheets

OTHER PUBLICATIONS

Anisimov, S. et al., "Discovering altered genomic expression patterns in heart: transcriptome determination by serial analysis of gene expression", *European Journal of Heart Failure,* 3, (2001), pp. 271–281.

Suzuki, T., et al., "Comprehensive gene expression profile of LPS–stimulated human monocytes by SAGE", *Blood,* 96, No. 7, (2000), pp. 2584–2591.

Inoue, H. et al., "Serial Analysis of Gene Expression in a Microglial Cell Line", *GLIA,* 28, (1999), pp. 266–271.

Chrast, R. et al., "The Mouse Brain Transcriptome by SAGE: Differences in Gene Expression between P30 Brains of the Partial Trisomy 16 Mouse Model of Down Syndrome (Ts65Dn) and Normals", *Genome Research,* 10(12), (2000), pp. 2006–2021.

* cited by examiner

SERIAL ANALYSIS OF TRANSCRIPT EXPRESSION USING MMEI AND LONG TAGS

This application claims the benefit of provisional application No. 60/221,556 filed Jul. 28, 2000 and No. 60/233,431 filed Sep. 18, 2000.

This invention was made with support from National Institutes of Health Grant Nos. CA43460 and CA57345. The Government retains certain rights in this invention.

FIELD OF THE INVENTION

The present invention relates generally to the field of gene and transcript expression and specifically to a method for the serial analysis of a large number of transcripts by identification of a defined region of a transcript which corresponds to a region of an expressed gene.

BACKGROUND OF THE INVENTION

Determination of the genomic sequence of higher organisms, including humans, is now a real and attainable goal. However, this analysis only represents one level of genetic complexity. The ordered and timely expression of genes represents another level of complexity equally important to the definition and biology of the organism.

The role of sequencing complementary DNA (cDNA), reverse transcribed from mRNA, as part of the human genome project has been debated as proponents of genomic sequencing have argued the difficulty of finding every mRNA expressed in all tissues, cell types, and developmental stages and have pointed out that much valuable information from intronic and intergenic regions, including control and regulatory sequences, will be missed by cDNA sequencing (Report of the Committee on Mapping and Sequencing the Human Genome, National Academy Press, Washington, D.C., 1988). Sequencing of transcribed regions of the genome using cDNA libraries has heretofore been considered unsatisfactory. Libraries of cDNA are believed to be dominated by repetitive elements, mitochondrial genes, ribosomal RNA genes, and other nuclear genes comprising common or housekeeping sequences. It is believed that cDNA libraries do not provide all sequences corresponding to structural and regulatory polypeptides or peptides (Putney, et al., Nature, 302:718, 1983).

Another drawback of standard cDNA cloning is that some mRNAs are abundant while others are rare. The cellular quantities of mRNA from various genes can vary by several orders of magnitude.

Techniques based on cDNA subtraction or differential display can be quite useful for comparing gene expression differences between two cell types (Hedrick, et al., Nature, 308:149, 1984; Liang and Pardee, Science, 257:967, 1992), but provide only a partial analysis, with no direct information regarding abundance of messenger RNA. The expressed sequence tag (EST) approach has been shown to be a valuable tool for gene discovery (Adams, et al., Science 252:1656, 1991; Adams, et al., Nature, 355:632, 1992; Okubo et al., Nature Genetics, 2:173, 1992), but like Northern blotting, RNase protection, and reverse transcriptase-polymerase chain reaction (RT-PCR) analysis (Alwine, et al., Proc. Natl. Acad Sci, U.S.A., 74:5350, 1977; Zinn et al, Cell, 34:865, 1983; Veres, et al., Science, 237:415, 1987), only evaluates a limited number of genes at a time. In addition, the EST approach preferably employs nucleotide sequences of 150 base pairs or longer for similarity searches and mapping.

Sequence tagged sites (STSs) (Olson, et al., Science, 245:1434, 1989) have also been utilized to identify genomic markers for the physical mapping of the genome. These short sequences from physically mapped clones represent uniquely identified map positions in the genome. In contrast, the identification of expressed genes relies on expressed sequence tags which are markers for those genes actually transcribed and expressed in vivo.

The restriction enzyme MmeI is a class II restriction endonclease which is a monomeric protein of 101 kDa. It is derived from *Methylophilus methylotrophus*. MmeI has a pI of 7.85 and is active in the pH range of 6.5 to 10, with the optimum at 7 to 8. MmeI cleaves DNA 20/18 nucleotides 3' of the asymmetric recognition sequence (5'-TCCRAC-3'). See Tucholski et al., Gene, vol. 157, pp. 87–92, 1995.

There is a need for an improved method which allows rapid, detailed analysis of thousands of expressed genes and/or expressed transcripts for the investigation of a variety of biological applications, particularly for establishing the overall pattern of gene expression in different cell types or in the same cell type under different physiologic or pathologic conditions. Identification of different patterns of expression has several utilities, including the identification of appropriate therapeutic targets, candidate genes for gene therapy (e.g., gene replacement), tissue typing, forensic identification, mapping locations of disease-associated genes, and for the identification of diagnostic and prognostic indicator genes. There is a need in the art for more efficient methods of accomplishing these taks. There is a need in the art for methods of determining correspondence between isolated nucleic acids and genes and/or expressed transcripts identified in genomic databases. There is a need in the art for methods of identifying rare expressed genes not otherwise predicted as well as for identifying non-translated RNA factors. There is a need in the art for additional tools to assist in assigning function to genes identified in the human genome.

SUMMARY OF THE INVENTION

The present invention provides a method for the rapid analysis of numerous transcripts in order to identify the overall pattern of transcript expression (transcriptome) in different cell types or in the same cell type under different physiologic, developmental or disease conditions. The method is based on the identification of a "long" nucleotide sequence tag at a defined position in a messenger RNA. The tag is used to identify the corresponding transcript and/or gene from which it was transcribed. By utilizing dimerized tags, termed a "ditag", the method of the invention allows elimination of certain types of bias which might occur during cloning and/or amplification and possibly during data evaluation. Concatemerization of these nucleotide sequence tags allows the efficient analysis of transcripts in a serial manner by sequencing multiple tags on a single DNA molecule, for example, a DNA molecule inserted in a vector or in a single clone.

The method described herein is the serial analysis of transcript expression, an approach which allows the analysis of a large number of transcripts. To demonstrate this strategy, cDNA sequence tags were generated from mRNA, randomly paired to form ditags, concatenated, and cloned. Manual sequencing of 1,000 tags revealed a characteristic gene expression pattern. Identification of such patterns is important diagnostically and therapeutically, for example. Moreover, the use of serial analysis as a transcript discovery tool was documented by the identification and isolation of new pancreatic corresponding to novel tags. This method provides a broadly applicable means for the quantitative cataloging and comparison of expressed transcripts in a variety of normal, developmental, and disease states. "Long SAGE" of "Long SATE" permits the ready and accurate identification of isolated tags with genomic sequence data.

DESCRIPTION OF THE PREFERRED EMBODIMENTS

Figure 1A:
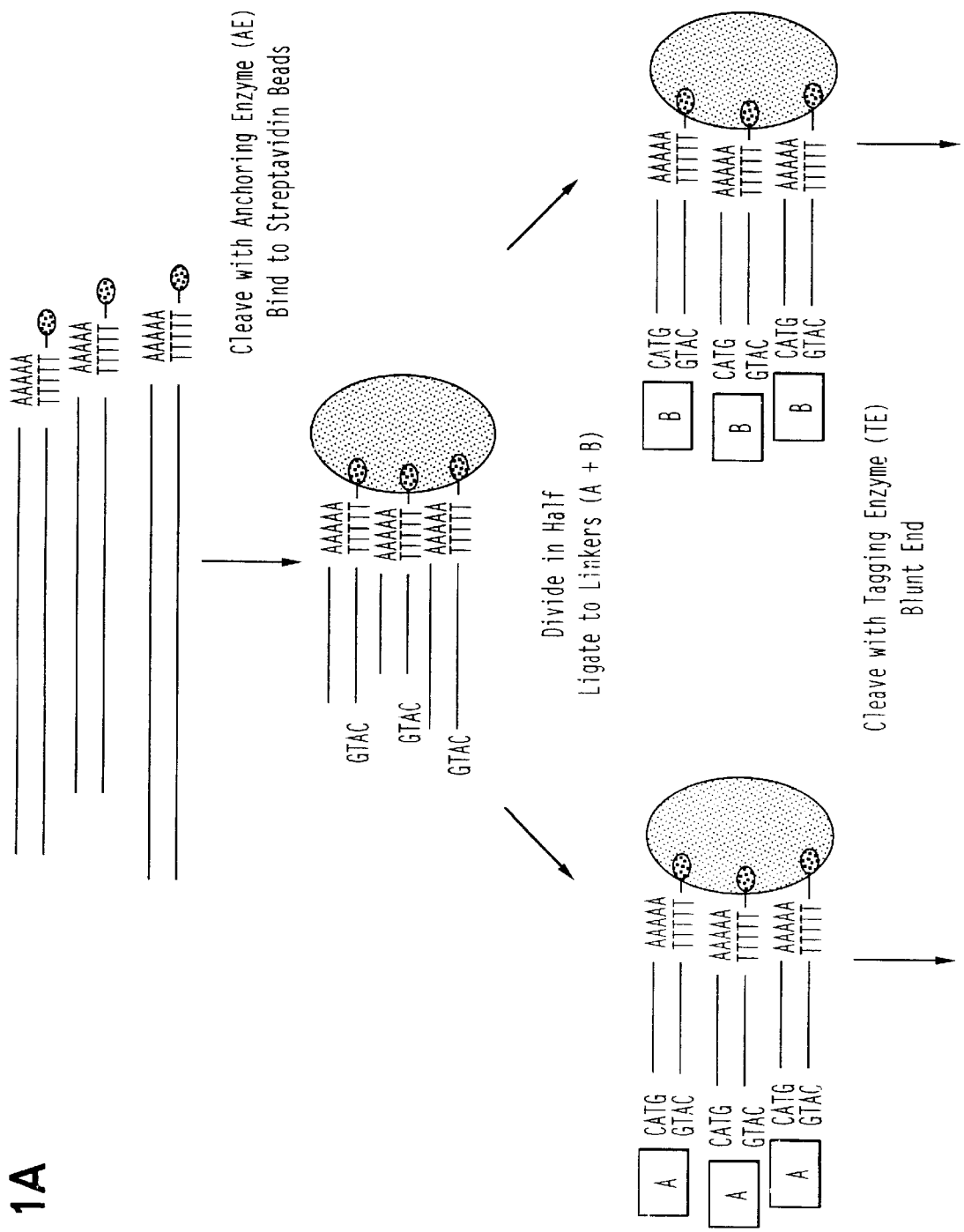
FIGS. 1A & 1B shows a schematic of SAGE. The first restriction enzyme, or anchoring enzyme, is NlaIII and the second enzyme, or tagging enzyme, is FokI in this example. Sequences represent primer derived sequences, and transcript derived sequences with "X" and "O" representing nucleotides of different tags. A tag attached to a tagging enzyme and an anchoring enzyme (SEQ ID NO: 25,) a ditag (SEQ ID NO: 26) and a concatamer of a ditag (SEQ ID NO: 27) are shown.

The present invention provides an improvement to the SAGE technique described in U.S. Pat. Nos. 5,695,937 and 5,866,330. The SAGE technique as it was originally taught and as it has been subsequently consistently practiced, uses the type IIS restriction endonuclease BsmFI as the "tagging enzyme".[1] It has now been found that longer tags of 20–22 nucleotides can be made which provide sufficient information to uniquely identify genomic sequences in the human genome. Surprisingly, not only genes expressed as protein can be identified, but also biologically active transcribed RNA which is not translated. Genomic regions that were previously thought to represent the non-coding strand may also be identified as transcriptionally active. Using MmeI as the tagging enzyme, 3' overhanging ends are formed. These ends can be ligated without removal of the overhanging ends and surprisingly this provides not only longer tags but also increased efficiency of ditag formation.

[1] Velculescu et al., Science 270:484–487, 1995; Virlon et al., PNAS 96:15286–15291, 1999; Angelastro et al., PNAS 97:10424–10429, 2000, Wang et al. PNAS 95: 11909–11914, 1998, Lee et al., PNAS 98:3340–3345, 2001; Sun et al., British Journal of Psychiatry 178: s137–s141, 2001; Hashimoto et al., Blood 96:2206–2214, 2000; Takano et al., British J. Cancer 83:1495–1502, 2000; Boon et al., EMBO J. 20:1383–1393, 2001; Matsumara et al., Plant J. 20:719–726, 1999; Ryo et al., FEBS Lett. 462:182–186, 1999; Anisimov et al., Eur. J. Heart Failure 3:271–281, 2001; Suzuki et al., Blood 96:2584–2591, 2000; Inoue et al., Glia 28:165–171, 1999; Chrast et al., Genome Research 10:2006–2021, 2000.

Using longer tags, we have identified genomic sequences which were previously not identified as transcribed. For example, sequences have been identified as transcribed which appear to be the reverse strand of known genes. Because the tags can be matched to human genomic sequences, RT-PCR primers can be designed from the matched human genomic sequences. Thus confirmation of the biological relevance of the reverse strand transcripts has been obtained.

Long tags that match sequences on the opposite strand of previously annotated or predicted transcripts can be tested for their validity by using the following protocol. Genomic sequence data is obtained for approximately 200 base pairs surrounding the SAGE tag (100 base pairs on both the 5' and 3' ends). Primers of 20 base pairs derived from sense (coding strand of the previously annotated transcript) and antisense strands are designed to PCR amplify a region approximately 100 base pairs long, inclusive of the SAGE tag. Source RNA (any RNA derived from specific tissue or cells expected to encode the reverse strand transcript) is reverse transcribed, in the presence or absence of reverse transcriptase (RT) into first strand cDNA using the sense primer. PCR reactions are performed on the first strand cDNA. Amplification of a specific DNA band of appropriate size from the sense-primed (+RT) cDNA suggests the existence of an authentic reverse strand transcript so long as the sense-primed (–RT) cDNA does not also produce the same size DNA band.

SAGE is a rapid, quantitative process for determining the abundance and nature of transcripts corresponding to expressed genes. SAGE is based on the identification of and characterization of partial, defined sequences of transcripts corresponding to gene segments. These defined transcript sequence "tags" are markers for genes which are expressed in a cell, a tissue, or an extract, for example.

SAGE is based on several principles. First, as has now been amply demonstrated, a short nucleotide sequence tag (9 to 10 bp) contains sufficient information content to uniquely identify a transcript, for example, from a database of cDNAs, provided it is isolated from a defined position within the transcript. For example, a sequence as short as 9 bp can distinguish 262,144 transcripts ($4^9$) given a random nucleotide distribution at the tag site, whereas estimates suggest that the human genome encodes about 80,000 to 200,000 transcripts (Fields, et al., Nature Genetics, 7:345 1994). The size of the tag can be shorter for lower eukaryotes or prokaryotes, for example, where the number of transcripts encoded by the genome is lower. For example, a tag as short as 6–7 bp may be sufficient for distinguishing transcripts in yeast. However, such short tags are typically not sufficient for identifying sequences in a human genomic database. According to the present invention, however, longer tags are obtained which are particularly useful for matching to genomic databases. Tags as long as 17–19, 19–21, 22–25, 26–30 nucleotides can be generated which provide sufficient information to uniquely identify a genomic human sequence, for example. As shown in TABLE 4, a 21-nucleotide tag has a 99.83% chance of identifying a unique sequence in the human genome.

Second, random dimerization of tags allows a procedure for reducing bias (caused by amplification and/or cloning). Third, concatenation of these sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. All of these principles may be applied independently, in combination, or in combination with other known methods of sequence identification.

SAGE provides a method for the detection of gene expression in a particular cell or tissue, or cell extract, for example, including at a particular developmental stage or in a particular disease state. The method comprises producing complementary deoxyribonucleic acid (cDNA) oligonucleotides, isolating a first defined nucleotide sequence tag from a first cDNA oligonucleotide and a second defined nucleotide sequence tag from a second cDNA oligonucleotide, linking the first tag to a first oligonucleotide linker, wherein the first oligonucleotide linker comprises a first sequence for hybridization of an amplification primer and linking the second tag to a second oligonucleotide linker, wherein the second oligonucleotide linker comprises a second sequence for hybridization of an amplification primer, and determining the nucleotide sequence of the tag(s), wherein the tag(s) correspond to an expressed gene. Preferably the linkers are distinct to eliminate the possibility of formation of hairpin loops.

Figure 1B:
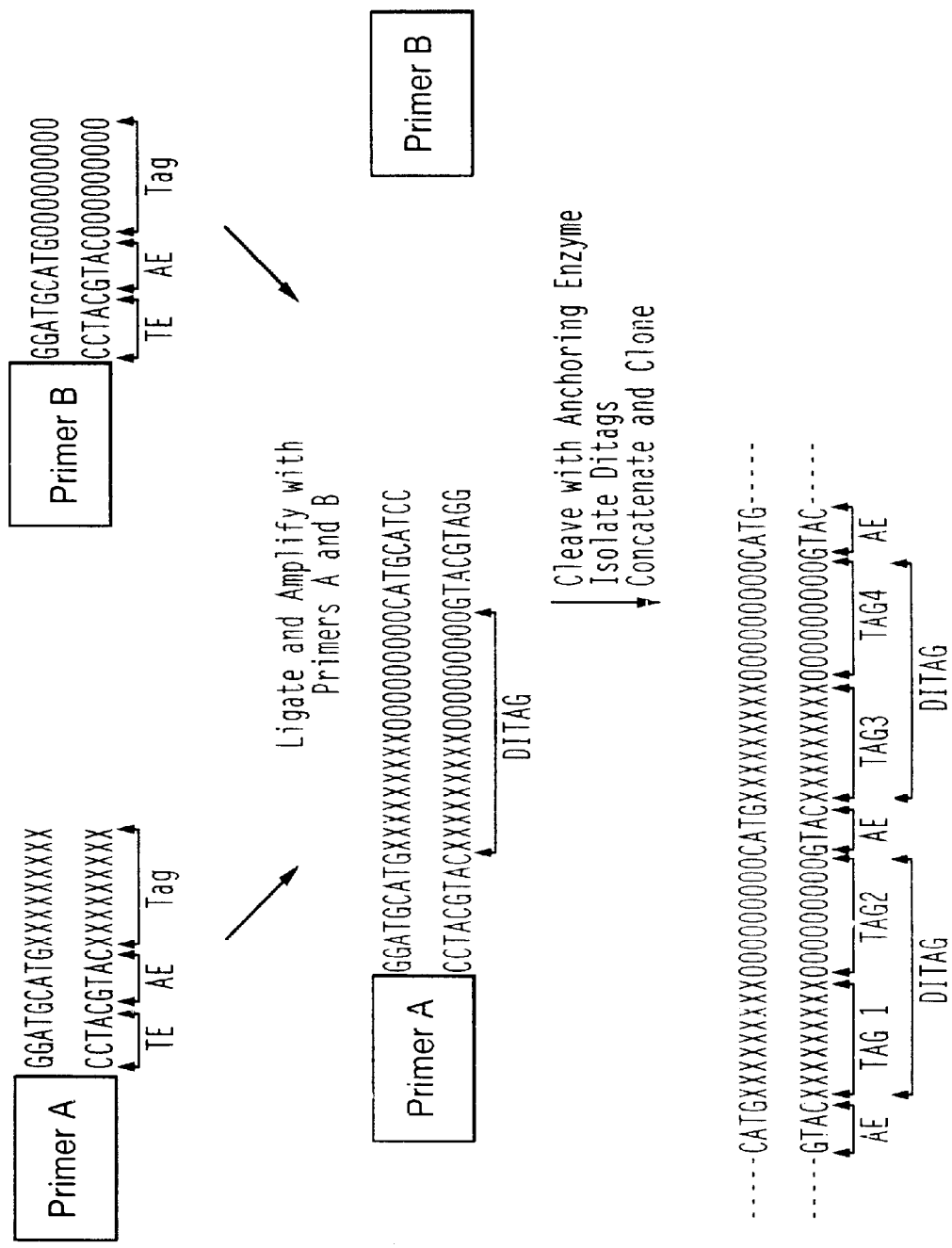

FIGS. 1A & 1B shows a schematic representation of the analysis of messenger RNA (mRNA) using SAGE as described in the method of the invention. mRNA is isolated from a cell or tissue of interest for in vitro synthesis of a double-stranded DNA sequence by reverse transcription of the mRNA. The double-stranded DNA complement of mRNA formed is referred to as complementary (cDNA).

The term "oligonucleotide" as used herein refers to primers or oligomer fragments comprised of two or more deoxyribonucleotides or ribonucleotides, preferably more than three. The exact size will depend on many factors, which in turn depend on the ultimate function or use of the oligonucleotide.

The method further includes ligating the first tag linked to the first oligonucleotide linker to the second tag linked to the second oligonucleotide linker and forming a "ditag". Each ditag represents two defined nucleotide sequences of at least one transcript, representative of at least one gene. Typically, a ditag represents two transcripts from two distinct genes. The presence of a defined cDNA tag within the ditag is indicative of expression of a gene having a sequence of that tag. The first tag linked to the first oligonucleotide linker and the second tag linked to the second oligonucleotide linker can be ligated directly using overhanging ends if they are formed by the tagging enzyme. The ends can also be trimmed-back using an exonuclease to form blunt ends for blunt ended ligation. It has been found that ligation of 2 bp 3'-overhanging ends formed using MmeI is significantly more efficient than the blunt-end ligation previously employed in conventional SAGE. We have found that using such overhanging ends that there is less contamination by linker sequences in the ditags. Thus when tags are concatamerized and/or cloned, a higher yield of information is achieved because there are more tags per clone and more relevant sequence on a per nucleotide basis.

The analysis of ditags, formed prior to any amplification step, provides a means to eliminate potential distortions introduced by amplification, e.g., PCR. The pairing of tags for the formation of ditags is a random event. The number of different tags is expected to be large, therefore, the probability of any two tags being coupled in the same ditag is small, even for abundant transcripts. Therefore, repeated ditags potentially produced by biased standard amplification and/or cloning methods are excluded from analysis by the method of the invention.

The term "defined" nucleotide sequence, or "defined" nucleotide sequence tag, refers to a nucleotide sequence derived from either the 5' or 3' terminus of a transcript. The sequence is defined by cleavage with a first restriction endonuclease, and represents nucleotides either 5' or 3' of the first restriction endonuclease site, depending on which terminus is used for capture (e.g., 3' when oligo-dT is used for capture as described herein).

As used herein, the terms "restriction endonucleases" and "restriction enzymes" refer to bacterial enzymes which bind to a specific double-stranded DNA sequence termed a recognition site or recognition nucleotide sequence, and cut double-stranded DNA at or near the specific recognition site.

The first endonuclease, termed "anchoring enzyme" or "AE" in FIG. 1, is selected by its ability to cleave a transcript at least one time and therefore produce a defined sequence tag from either the 5' or 3' end of a transcript. Preferably, a restriction endonuclease having at least one recognition site and therefore having the ability to cleave a majority of cDNAs is utilized. For example, as illustrated herein, enzymes which have a 4 base pair recognition site are expected to cleave every 256 base pairs ($4^4$) on average while most transcripts are considerably larger. Restriction endonucleases which recognize a 4 base pair site include NlaIII, as exemplified in the EXAMPLES of the present invention. Other similar endonucleases having at least one recognition site within a DNA molecule (e.g., cDNA) will be known to those of skill in the art (see for example, Current Protocols in Molecular Biology, Vol. 2, 1995, Ed. Ausubel, et al., Greene Publish. Assoc. & Wiley Interscience, Unit 3.1.15; New England Biolabs Catalog, 1995).

After cleavage with the anchoring enzyme, the most 5' or 3' region of the cleaved cDNA can then be isolated by binding to a capture medium. For example, as illustrated in the present EXAMPLES, streptavidin beads are used to isolate the defined 3' nucleotide sequence tag when the oligo dT primer for cDNA synthesis is biotinylated. In this example, cleavage with the first or anchoring enzyme provides a unique site on each transcript which corresponds to the restriction site located closest to the poly-A tail. Likewise, the 5' cap of a transcript (the cDNA) can be utilized for labeling or binding a capture means for isolation of a 5' defined nucleotide sequence tag. Those of skill in the art will know other similar capture systems (e.g., biotin/streptavidin, digoxigenin/anti-digoxigenin) for isolation of the defined sequence tag as described herein. Alternatively, the entire process can be carried out while cDNA is attached to a bead. In fact, the cDNA can be synthesized on the bead by binding mRNA to a bead which has one or more oligo (dT) molecules coated or attached and reverse transcribing the mRNA attached to the bead by hybridization via a poly(A) tract. Subsequent digestion with the anchoring enzyme can be done on the beads as well.

The invention is not limited to use of a single "anchoring" or first restriction endonuclease. It may be desirable to perform the method of the invention sequentially, using different enzymes on separate samples of a preparation, in order to identify a complete pattern of transcription for a cell or tissue. In addition, the use of more than one anchoring enzyme provides confirmation of the expression pattern obtained from the first anchoring enzyme. Therefore, it is also envisioned that the first or anchoring endonuclease may rarely cut cDNA such that few or no cDNA representing abundant transcripts are cleaved. Thus, transcripts which are cleaved represent "unique" transcripts. Restriction enzymes that have a 7–8 bp recognition site for example, would be enzymes that would rarely cut cDNA. Similarly, more than one tagging enzyme, described below, can be utilized in order to identify a complete pattern of transcription.

In one embodiment of the invention, classical SAGE data and long SAGE data are correlated. The classical and long SAGE methods use different tagging enzymes (or the same tagging enzyme used under different conditions) to generate different length tags. The classical and long SAGE can either use the same or different anchoring enzymes. If the same anchoring enzyme is used, the short tags will nest within the long tags. This is advantageous for using the large amount of expression data generated with short tags and linking it to the genome using the long tags. Thus the long tags serve to "anchor" the short tags to the genome. An example of such anchoring is shown below.

Ten DLD1 colon cancer SAGE short tags that do not match to any entries in Unigene (build132) are shown below. Long tag data from a long SATE analysis performed on DLD1 colon cancer cells was able to extend the given short tags. These 17 base tags are located uniquely within the human genome and fall within the gene descriptions noted.

sequence tag refers to the purification of the 5' or 3' tag from other cleaved cDNA.

In one embodiment, the isolated defined nucleotide sequence tags are separated into two pools of cDNA, when the linkers have different sequences. Each pool is ligated via the anchoring, or first restriction endonuclease site to one of two linkers. When the linkers have the same sequence, it is not necessary to separate the tags into pools. The first oligonucleotide linker comprises a first sequence for hybridization of an amplification primer and the second oligonucleotide linker comprises a second sequence for hybridization of an amplification primer. In addition, the linkers further comprise a second restriction endonuclease site, also termed the "tagging enzyme" or "TE". Long SATE employs a TE which cleaves at least 17, 18, 19, 20, or 21 nucleotides from its recognition site. The method of the invention does not require, but preferably comprises amplifying the ditag oligonucleotide after ligation.

The second restriction endonuclease (TE) cleaves at a site distant from or outside of the recognition site. For example, the second restriction endonuclease can be a type IIS restriction enzyme. Type IIS restriction endonucleases cleave at a defined distance up to 2–13 nt away from their 4–7 bp asymmetric recognition sites and include BbvI, BbvII, BinI, FokI, HgaI, HphI, MboII, MnlI, SfaNI, TaqII, Tth111II, as reviewed in Szybalski, W., Gene, 40:169, 1985. Examples of type IIS restriction endonucleases include BsmFI and FokI. Other similar enzymes will be known to those of skill in the art (see, Current Protocols in Molecular Biology, supra). A particularly preferred tagging enzyme, according to the invention is an enzyme which cleaves 20/18 nucleotides 3' of its recognition site forming 3' overhanging ends, such as MmeI. Any other suitable enzyme known in the art can be used. In addition, restriction endonucleases with desirable properties can be artificially evolved, i.e., subjected to selection and screening, to obtain an enzyme which is useful as a tagging enzyme for long SATE. Desirable enzymes

| Short Tag | Unigene Match | LongTag | Description |
|---|---|---|---|
| ATCACGCCCT (SEQ ID NO: 1) | None | ATCACGCCCTCATAATC (SEQ ID NO: 2) | Hypothetical protein |
| TCACCCAGGG (SEQ ID NO: 3) | None | TCACCCAGGGACCCATT (SEQ ID NO: 4) | Ribosomal protein S4. X-linked |
| TTGGTGATAC (SEQ ID NO: 5) | None | TTGGTGATACCCCCCGG (SEQ ID NO: 6) | RDBD |
| AAACAAATCA (SEQ ID NO: 7) | None | AAACAAATCACCATCCT (SEQ ID NO: 8) | KIAA0026 |
| CCGTGGTAGC (SEQ ID NO: 9) | None | CCGTGGTAGCCAATGTT (SEQ ID NO: 10) | Kinesin-related |
| GAAGGAGATG (SEQ ID NO: 11) | None | GAAGGAGATGGCGAAAG (SEQ ID NO: 12) | Hypothetical protein |
| GCCGCTCTC (SEQ ID NO: 13) | None | GCCGCTCTCCCGGACC (SEQ ID NO: 14) | Catenin-vinculin-related |
| TCTTACCATA (SEQ ID NO: 15) | None | TCTTACCATACACACTG (SEQ ID NO: 16) | Hypothetical protein |
| TGGATAATTC (SEQ ID NO: 17) | None | TGGATAATTCAAACAAA (SEQ ID NO: 18) | Hypothetical protein |
| TTCCAGCCAA (SEQ ID NO: 19) | None | TTCCAGCCAATGGATGA (SEQ ID NO: 20) | Hypothetical protein |

The term "isolated" as used herein includes polynucleotides substantially free of other nucleic acids, proteins, lipids, carbohydrates or other materials with which it is naturally associated. cDNA is not naturally occurring as such, but rather is obtained via manipulation of a partially purified naturally occurring mRNA. Isolation of a defined cleave at least 18–21 nucleotides distant from their recognition sites. Artificial restriction endonucleases can also be used. Such endonucleases are made by protein engineering. For example, the endonuclease FokI has been engineered by insertions so that it cleaves one nucleotide further away from its recognition site on both strands of the DNA substrates.

See Li and Chandrasegaran, *Proc. Nat. Acad. Sciences USA* 90:2764–8, 1993. Such techniques can be applied to generate restriction endonucleases with desirable recognition sequences and desirable distances from recognition site to cleavage site.

The first and second "linkers" which are ligated to the defined nucleotide sequence tags are oligonucleotides having the same or different nucleotide sequences. The linkers are designed so that cleavage of the ligation products with the second restriction enzyme, or tagging enzyme, results in release of the linker having a defined nucleotide sequence tag (e.g., 3' of the restriction endonuclease cleavage site as exemplified herein). The defined nucleotide sequence tag may be from about 6 to 30 base pairs. In classical SAGE, the tag is typically about 9 to 15 base pairs. In long SATE the tag is 19–30 base pairs. Therefore, a ditag is from about 12 to 60 base pairs, and preferably from 38 to 42 base pairs.

The pool of defined tags ligated to linkers having the same sequence, or the two pools of defined nucleotide sequence tags ligated to linkers having different nucleotide sequences, are randomly ligated to each other "tail to tail". The portion of the cDNA tag furthest from the linker is referred to as the "tail". The sticky tail ends formed by digestion with the tagging enzyme can in some cases be filled-in with a DNA polymerase or removed by nuclease digestion prior to ligation. Alternatively, no filling-in may be done. As illustrated in FIG. 1, the ligated tag pair, or ditag, has a first restriction endonuclease site upstream (5') and a first restriction endonuclease site downstream (3') of the ditag; a second restriction endonuclease cleavage site upstream and downstream of the ditag, and a linker oligonucleotide containing both a second restriction enzyme recognition site and an amplification primer hybridization site upstream and downstream of the ditag. In other words, the ditag is flanked by the first restriction endonuclease site, the second restriction endonuclease cleavage site and the linkers, respectively.

The ditag can be amplified by utilizing primers which specifically hybridize to one strand of each linker. Preferably, the amplification is performed by standard polymerase chain reaction (PCR) methods as described (U.S. Pat. No. 4,683,195). Alternatively, the ditags can be amplified by cloning in prokaryotic-compatible vectors or by other amplification methods known to those of skill in the art.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. In the present invention, the primers can be substantially or completely complementary to the oligonucleotide linkers.

Cleavage of the amplified PCR product with the first restriction endonuclease allows isolation of ditags which can be concatenated by ligation. After ligation, it may be desirable to clone the concatemers, although it is not required in the method of the invention. Analysis of the ditags or concatemers, whether or not amplification was performed, is by standard sequencing methods. Concatemers generally consist of about 2 to 200 ditags and preferably from about 8 to 20 ditags. While these are preferred concatemers, it will be apparent that the number of ditags which can be concatenated will depend on the length of the individual tags and can be readily determined by those of skill in the art without undue experimentation. After formation of concatemers, multiple tags can be cloned into a vector for sequence analysis, or Iternatively, ditags or concatemers can be directly sequenced without cloning by methods known to those of skill in the art.

Among the standard procedures for cloning the defined nucleotide sequence tags of the invention is insertion of the tags into vectors such as plasmids or phage. The ditag or concatemers of ditags produced by the method described herein are cloned into recombinant vectors for further analysis, e.g., sequence analysis, plaque/plasmid hybridization using the tags as probes, by methods known to those of skill in the art.

The term "recombinant vector" refers to a plasmid, virus or other vehicle known in the art that has been manipulated by insertion or incorporation of the ditag genetic sequences. Such vectors contain a promoter sequence which facilitates the efficient transcription of the a marker genetic sequence for example. The vector typically contains an origin of replication, a promoter, as well as specific genes which allow phenotypic selection of the transformed cells. Vectors suitable for use in the present invention include for example, pBlueScript (Stratagene, La Jolla, Calif.); pBC, pSL301 (Invitrogen) and other similar vectors known to those of skill in the art. Preferably, the ditags or concatemers thereof are ligated into a vector for sequencing purposes.

Vectors in which the ditags are cloned can be transferred into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Transformation of a host cell with a vector containing ditag(s) may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed by electroporation or other commonly used methods in the art.

The ditags present in a particular clone can be sequenced by standard methods (see for example, Current Protocols in Molecular Biology, supra, Unit 7) either manually or using automated methods.

In another embodiment, the present invention provides a kit useful for detection of gene expression wherein the presence of a defined nucleotide tag or ditag is indicative of expression of a gene having a sequence of the tag. The kit comprises: a first container containing an oligonucleotide linker having a sequence useful for hybridization to an amplification primer; the oligonucleotide linker further comprises a restriction endonuclease recogition site for an enzyme which cleaves 18–20 nucleotides distant from its recognition sequence; and a second container having a nucleic acid primer for hybridization to the oligonucleotide linker. Other containers may comprise the restriction endonuclease and/or a DNA polymerase for amplification. A particularly preferred retriction endonuclease is MmeI, an enzyme which forms 3' overhanging ends.

In yet another embodiment, the invention provides an oligonucleotide concatamer having at least two defined nucleotide sequence tags, wherein at least one of the sequence tags corresponds to at least one expressed gene. The concatamer consists of about 1 to 200 ditags, and preferably about 8 to 20 ditags. Such concatamers are useful for the analysis of gene expression by identifying the defined nucleotide sequence tag corresponding to an expressed gene in a cell, tissue or cell extract, for example.

It is envisioned that the identification of differentially expressed transcripts using the SATE technique of the invention can be used in combination with other genomics techniques. For example, individual tags, and preferably ditags, can be hybridized with oligonucleotides immobilized on a solid support (e.g., nitrocellulose filter, glass slide, silicon chip). Such techniques include "parallel sequence analysis" or PSA, as described below. The sequence of the ditags formed by the method of the invention can also be determined using limiting dilutions by methods including clonal sequencing (CS).

Briefly, PSA is performed after ditag preparation, wherein the oligonucleotide sequences to which the ditags are hybridized are preferably unlabeled and the ditag is preferably detectably labeled. Alternatively, the oligonucleotide can be labeled rather than the ditag. The ditags can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the ditag, or will be able to ascertain such, using routine experimentation. For example, PCR can be performed with labeled (e.g., fluorescein tagged) primers. Preferably, the ditag contains a fluorescent end label.

The labeled or unlabeled ditags are separated into single-stranded molecules which are preferably serially diluted and added to a solid support (e.g., a silicon chip as described by Fodor, et al., Science, 251:767, 1991) containing oligonucleotides representing, for example, every possible permutation of a 10-mer (e.g., in each grid of a chip). The solid support is then used to determine differential expression of the tags contained within that support (e.g., on a grid on a chip) by hybridization of the oligonucleotides on the solid support with tags produced from cells under different conditions (e.g., different stage of development, growth of cells in the absence and presence of a growth factor, normal versus transformed cells, comparison of different tissue expression, etc). In the case of fluoresceinated end labeled ditags, analysis of fluorescence is indicative of hybridization to a particular 10-mer. When the immobilized oligonucleotide is fluoresceinated for example, a loss of fluorescence due to quenching (by the proximity of the hybridized ditag to the labeled oligo) is observed and is analyzed for the pattern of gene expression. An illustrative example of the method is shown in Example 4 herein.

The SATE method of the invention is also useful for clonal sequencing, similar to limiting dilution techniques used in cloning of cell lines. For example, ditags or concatemers thereof, are diluted and added to individual receptacles such that each receptacle contains less than one DNA molecule per receptacle. DNA in each receptacle is amplified and sequenced by standard methods known in the art, including mass spectroscopy. Assessment of differential expression is performed as described above for SAGE.

Those of skill in the art can readily determine other methods of analysis for ditags or individual tags produced by SATE as described in the present invention, without resorting to undue experimentation. The concept of deriving a defined tag from a sequence in accordance with the present invention is useful in matching tags of samples to a sequence database, in particular a database of genomic sequences, such as humans, mice, cows, pigs, horses, etc. In the preferred embodiment, a computer method is used to match a sample sequence with known sequences.

Figure 5A:
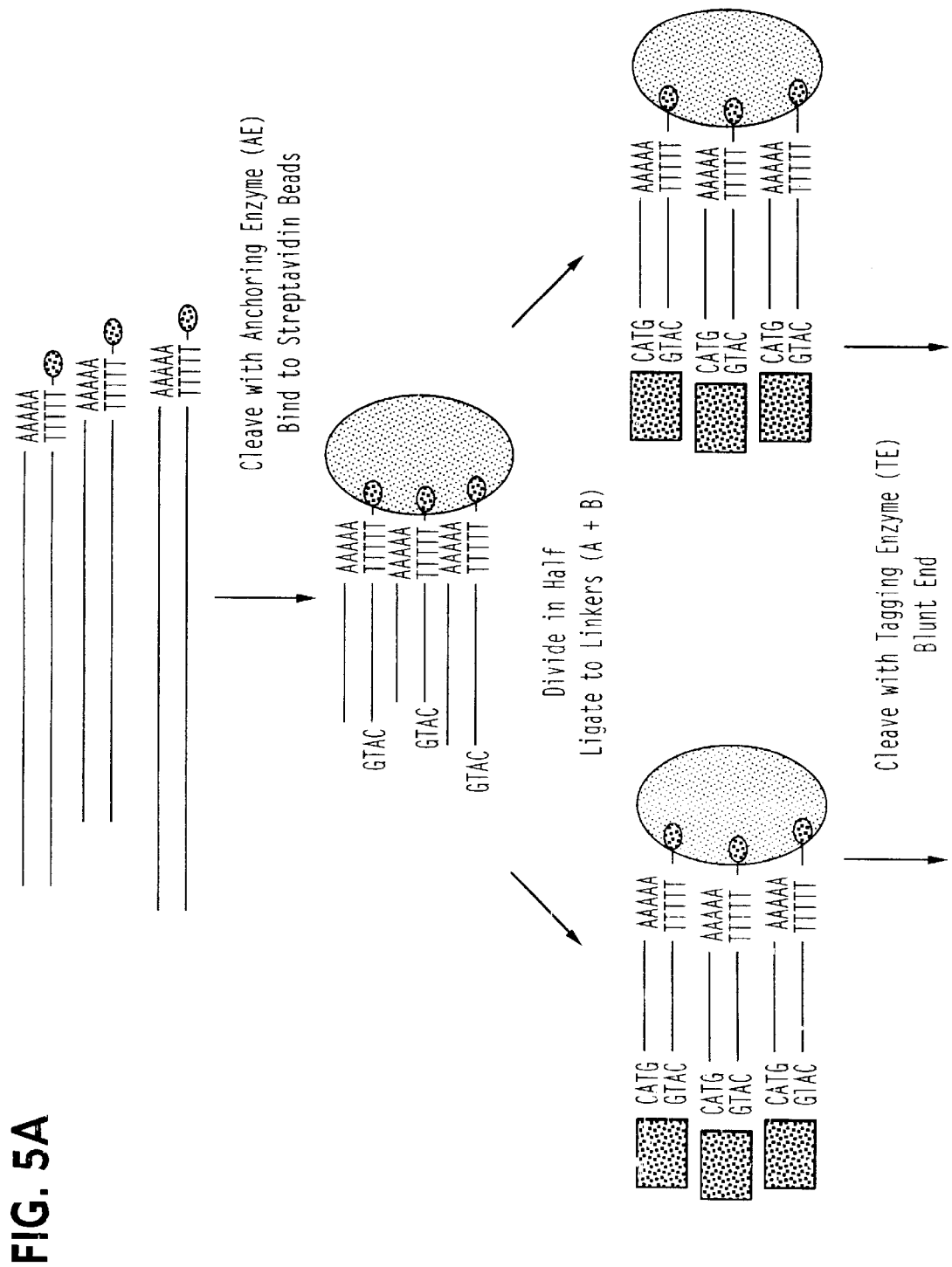
FIG. 5 shows a schematic of Long SAGE. The first restriction enzyme, or anchoring enzyme (AE) is NlaIII, and the second enzyme, or tagging enzyme (TE) is MmeI in this example. Sequences represent primer derived sequences, and transcript derived sequences are represented with "X" and "O" representing nucleotides of different tags. A tag attached to a tagging enzyme and an anchoring enzyme (SEQ ID NO: 28,) a ditag (SEQ ID NO: 29) and a concatamer of a ditag (SEQ ID NO: 30) are shown.
Figure 5B:
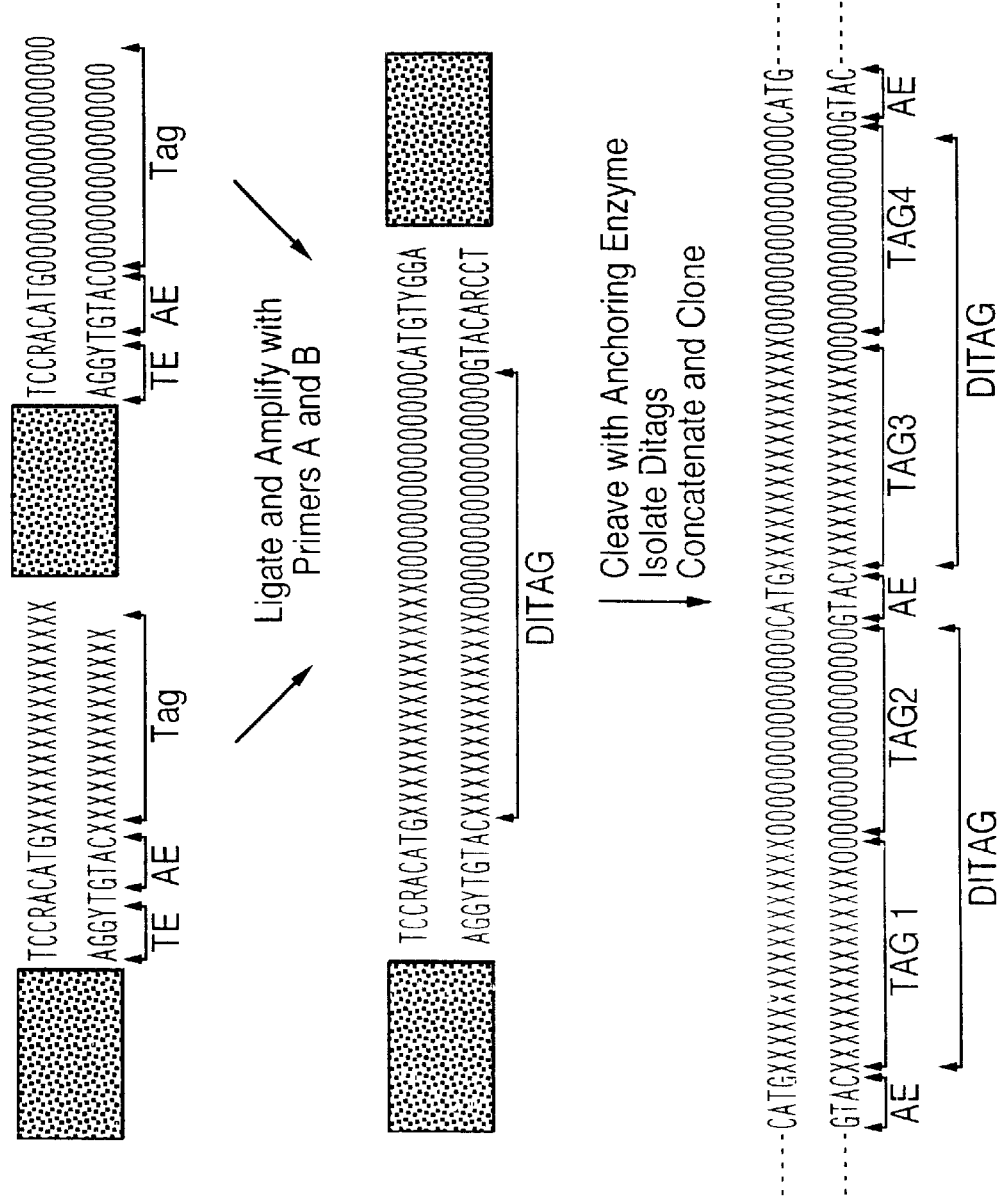
Figure 6:
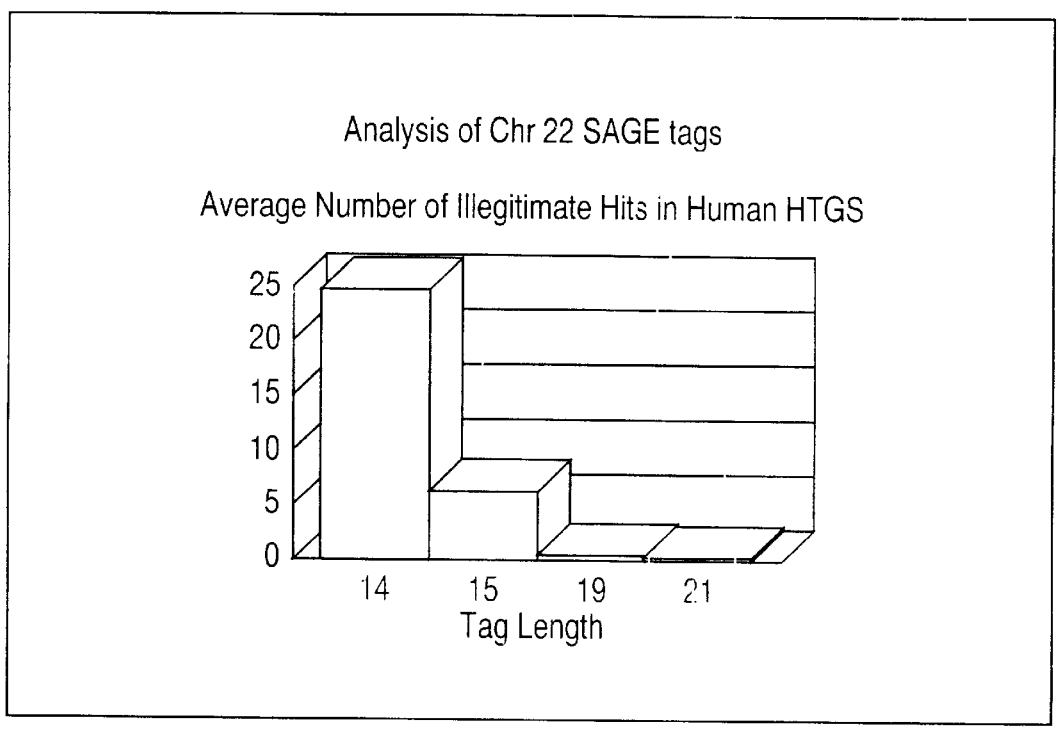
FIG. 6 shows an analysis of chromosome 22 SAGE tags. As shown in the bar graph, as the length of the tag increases the accuracy of the process of matching a SAGE tag to a genomic database increases dramatically. Tags in the range of 19–21 nucleotides are extemely accurate for matching to a genomic database. See also Table 4 which provides theoretical probabilities that a tag is unique in the human genome based on its size.

One of the primary strengths of using a restriction endonuclease as a tagging enzyme which cuts at least 17 or 18 nucleotides distant from its recognition site is the ability to unambiguously identify a location in the genome from which a long tag is derived. Thus, it is significantly easier and more accurate to determine the identity of the gene or genomic region that gave rise to a tag, particularly if one is dealing with an organism for which significant genomic data but only limited cDNA sequence information is available. Table 4 shows a computation of the probability that tags of differing length will be unique in the human genome. In addition, a comparison of the number of times long tags vs their cognate short tags "hit" the human genome is shown in FIG. 5. This analysis is based on theoretical tags derived from known genes on Chromosome 22.

In one embodiment, a sequence tag for a sample is compared to corresponding information in a sequence database to identify known sequences that match the sample sequence. Preferably the database is genomic sequence, more preferably human genomic sequence. One or more tags can be determined for each sequence in the sequence database as the N base pairs adjacent to each anchoring enzyme site within the sequence. However, in the preferred embodiment, only the first anchoring enzyme site from the 3' end is used to determine a tag. In the preferred embodiment, the adjacent base pairs defining a tag are on the 3' side of the anchoring enzyme site, and N is preferably 9, 11, 13, 15, 17, 19, 21, 23, 25, 27, or 29.

A linear search through such a database may be used. However, in the preferred embodiment, a sequence tag from a sample is converted to a unique numeric representation by converting each base pair (A, C, G, or T) of an N-base tag to a number or "tag code" (e.g., A=0, C=1, G=2, T=3, or any other suitable mapping). A tag is determined for each sequence of a sequence database as described above, and the tag is converted to a tag code in a similar manner. In the preferred embodiment, a set of tag codes for a sequence database is stored in a pointer file. The tag code for a sample sequence is compared to the tag codes in the pointer file to determine the location in the sequence database of the sequence corresponding to the sample tag code. (Multiple corresponding sequences may exist if the sequence database has redundancies).

Figure 4:
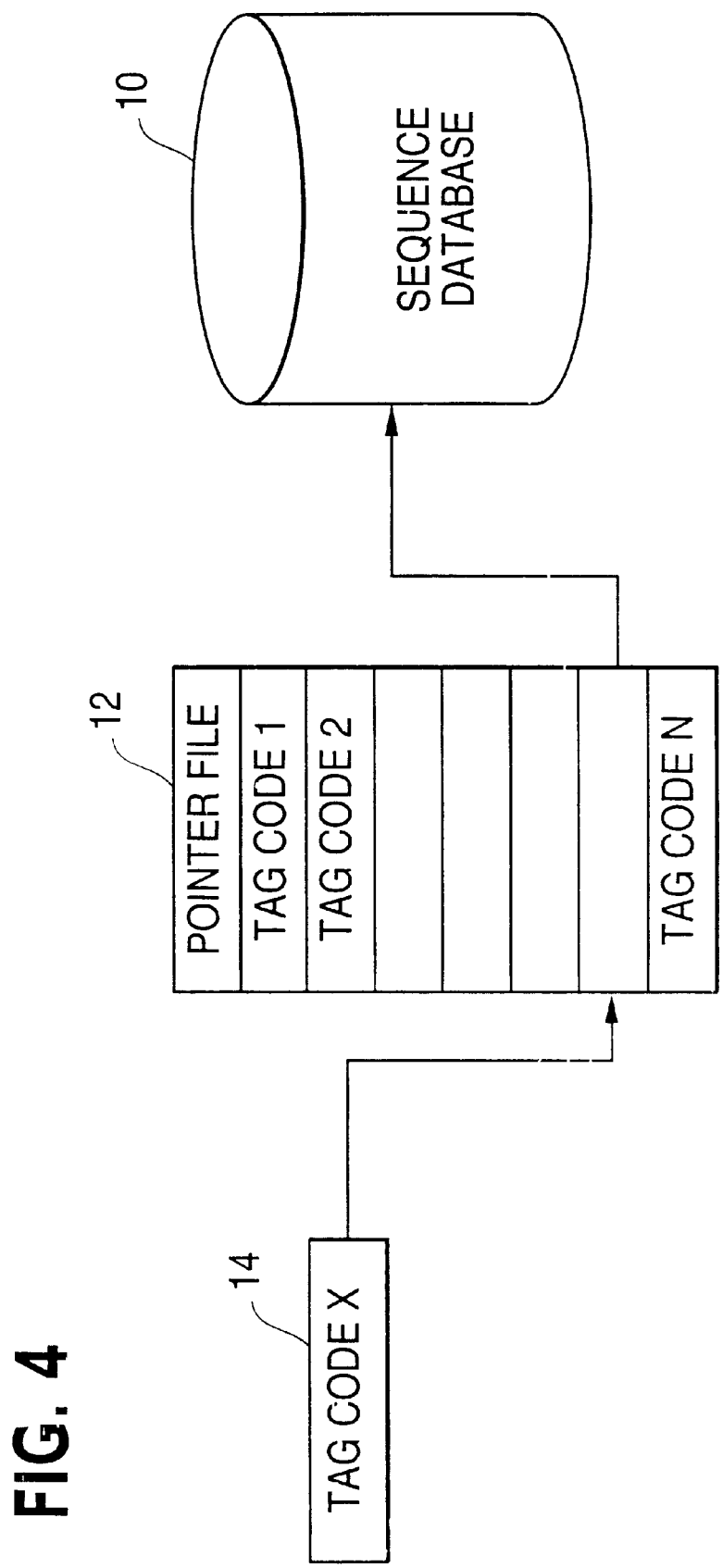
FIG. 4 is a block diagram of a tag code database access system in accordance with the present invention.

FIG. 4 is a block diagram of a tag code database access system in accordance with the present invention. A sequence database 10 (e.g., the Human Genome Sequence Database) is processed as described above, such that each sequence has a tag code determined and stored in a pointer file 12. A sample tag code X for a sample is determined as described above, and stored within a memory location 14 of a computer. The sample tag code X is compared to the pointer file 12 for a matching sequence tag code. If a match is found, a pointer associated with the matching sequence tag code is used to access the corresponding sequence in the sequence database 10.

The pointer file 12 may be in any of several formats. In one format, each entry of the pointer file 12 comprises a tag code and a pointer to a corresponding record in the sequence database 12. The sample tag code X can be compared to sequence tag codes in a linear search. Alternatively, the sequence tag codes can be sorted and a binary search used. As another alternative, the sequence tag codes can be structured in a hierarchical tree structure (e.g., a B-tree), or as a singly or doubly linked list, or in any other conveniently searchable data structure or format.

In the preferred embodiment, each entry of the pointer file 12 comprises only a pointer to a corresponding record in the sequence database 10. In building the pointer file 12, each sequence tag code is assigned to an entry position in the pointer file 12 corresponding to the value of the tag code. For example, if a sequence tag code was "1043", a pointer to the corresponding record in the sequence database 10 would be stored in entry #1043 of the pointer file 12. The value of a sample tag code X can be used to directly address the location in the pointer file 12 that corresponds to the sample tag code X, and thus rapidly access the pointer stored in that location in order to address the sequence database 10.

Because only four values are needed to represent all possible base pairs, using binary coded decimal (BCD) numbers for tag codes in conjunction with the preferred pointer file 12 structure leads to a "sparse" pointer file 12 that wastes memory or storage space. Accordingly, the present invention transforms each tag code to number base 4 (i.e., 2 bits per code digit), in known fashion, resulting in a compact pointer file 12 structure. For example, for tag sequence "AGCT", with $A=00_2$, $C=01_2$, $G=10_2$, $T=11_2$, the base four representation in binary would be "00011011".

In contrast, the BCD representation would be "00000000 00000001 00000010 000000011". Of course, it should be understood that other mappings of base pairs to codes would provide equivalent function.

The concept of deriving a defined tag from a sample sequence in accordance with the present invention is also useful in comparing different samples for similarity. In the preferred embodiment, a computer method is used to match sequence tags from different samples. For example, in comparing materials having a large number of sequences (e.g., tissue), the frequency of occurrence of the various tags in a first sample can be mapped out as tag codes stored in a distribution or histogram-type data structure. For example, a table structured similar to pointer file 12 in FIG. 4 can be used where each entry comprises a frequency of occurrence value. Thereafter, the various tags in a second sample can be generated, converted to tag codes, and compared to the table by directly addressing table entries with the tag code. A count can be kept of the number of matches found, as well as the location of the matches, for output in text or graphic form on an output device, and/or for storage in a data storage system for later use.

The tag comparison aspects of the invention may be implemented in hardware or software, or a combination of both. Preferably, these aspects of the invention are implemented in computer programs executing on a programmable computer comprising a processor, a data storage system (including volatile and non-volatile memory and/or storage elements), at least one input device, and at least one output device. Data input through one or more input devices for temporary or permanent storage in the data storage system includes sequences, and may include previously generated tags and tag codes for known and/or unknown sequences. Program code is applied to the input data to perform the functions described above and generate output information. The output information is applied to one or more output devices, in known fashion.

Each such computer program is preferably stored on a storage media or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

The following examples are intended to illustrate but not limit the invention. While they are typical of those that might be used, other procedures known to those skilled in the art may alternatively be used.

EXAMPLES

For exemplary purposes, the SAGE method of the invention was used to characterize gene expression in the human pancreas. NlaIII was utilized as the first restriction endonuclease, or anchoring enzyme, and BsmFI as the second restriction endonuclease, or tagging enzyme, yielding a 9 bp tag (BsmFI was predicted to cleave the complementary strand 14 bp 3' to the recognition site GGGAC and to yield a 4 bp 5' overhang (New England BioLabs). Overlapping the BsmFI and NlaIII (CATG) sites as indicated (GGGACATG) would be predicted to result in a 11 bp tag. However, analysis suggested that under the cleavage conditions used (37. degree. C.), BsmFI often cleaved closer to its recognition site leaving a minimum of 12 bp 3' of its recognition site. Therefore, only the 9 bp closest to the anchoring enzyme site was used for analysis of tags. Cleavage at 65. degree. C. results in a more consistent 11 bp tag.

Computer analysis of human transcripts from Gen Bank indicated that greater than 95% of tags of 9 bp in length were likely to be unique and that inclusion of two additional bases provided little additional resolution. Human sequences (84,300) were extracted from the GenBank 87 database using the Findseq program provided on the IntelliGenetics Bionet on-line service. All further analysis was performed with a SAGE program group written in Microsoft Visual Basic for the Microsoft Windows operating system. The SAGE database analysis program was set to include only sequences noted as "RNA" in the locus description and to exclude entries noted as "EST", resulting in a reduction to 13,241 sequences. Analysis of this subset of sequences using NlaIII as anchoring Enzyme indicated that 4,127 nine bp tags were unique while 1,511 tags were found in more than one entry. Nucleotide comparison of a randomly chosen subset (100) of the latter entries indicated that at least 83% were due to redundant data base entries for the same gene or highly related genes (>95% identity over at least 250 bp). This suggested that 5381 of the 9 bp tags (95.5%) were unique to a transcript or highly conserved transcript family. Likewise, analysis of the same subset of GenBank with an 11 bp tag resulted only in a 6% decrease in repeated tags (1511 to 1425) instead of the 94% decrease expected if the repeated tags were due to unrelated transcripts.

Example 1

As outlined above, mRNA from human pancreas was used to generate ditags. Briefly, five ug mRNA from total pancreas (Clontech) was converted to double stranded cDNA using a BRL cDNA synthesis kit following the manufacturer's protocol, using the primer biotin-5'$T_{18}$-3'. The cDNA was then cleaved with NlaIII and the 3' restriction fragments isolated by binding to magnetic streptavidin beads (Dynal). The bound DNA was divided into two pools, and one of two linkers was ligated to each pool.

After extensive washing to remove unligated linkers, the linkers and adjacent tags were released by cleavage with BsmFI. The resulting overhangs were filled in with T4 polymerase and the pools combined and ligated to each other. The desired ligation product was then amplified for 25 cycles. The PCR reaction was then analyzed by polyacrylamide gel electrophoresis and the desired product excised. An additional 15 cycles of PCR were then performed to generate sufficient product for efficient ligation and cloning.

The PCR ditag products were cleaved with NlaIII and the band containing the ditags was excised and self-ligated. After ligation, the concatenated ditags were separated by polyacrylamide gel electrophoresis and products greater than 200 bp were excised. These products were cloned into the SphI site of pSL301 (Invitrogen). Colonies were screened for inserts by PCR using T7 and T3 sequences outside the cloning site as primers. Clones containing at least 10 tags (range 10 to 50 tags) were identified by PCR amplification and manually sequenced as described (Del Sal, et al., Biotechniques 7:514, 1989). Sequence files were analyzed using the SAGE software group which identifies the anchoring enzyme site with the proper spacing and extracts the two intervening tags and records them in a database. The 1,000 tags were derived from 413 unique ditags and 87 repeated ditags. The latter were only counted once to eliminate potential PCR bias of the quantitation. The function of SAGE software is merely to optimize the search for gene sequences.

Table 1 shows analysis of the first 1,000 tags. Sixteen percent were eliminated because they either had sequence ambiguities or were derived from linker sequences. The remaining 840 tags included 351 tags that occurred once and 77 tags that were found multiple times. Nine of the ten most abundant tags matched at least one entry in GenBank R87. The remaining tag was subsequently shown to be derived from amylase. All ten transcripts were derived from genes of known pancreatic function and their prevalence was consistent with previous analyses of pancreatic RNA using conventional approaches (Han, et al., Proc. Natl. Acad. Sci. U.S.A. 83:110, 1986; Takeda, et al., Hum. Mol. Gen., 2:1793, 1993).

TABLE 1

Pancreatic SAGE Tags

| Tag | Gene | N | Percent |
|---|---|---|---|
| GAGCACACC | Procarboxypeptidase A1 (X67318) | 64 | 7.6 |
| TTCTGTGTG | Pancreatic Trypsinogen 2 (M27602) | 46 | 5.5 |
| GAACACAAA | Chymotrypsinogen (M24400) | 37 | 4.4 |
| TCAGGGTGA | Pancreatic Trypsin 1 (M22612) | 31 | 3.7 |
| GCGTGACCA | Elastase 111B (M18692) | 20 | 2.4 |
| GTGTGTGCT | Protease E (D00306) | 16 | 1.9 |
| TCATTGGCC | Pancreatic Lipase (M93285) | 16 | 1.9 |
| CCAGAGAGT | Procarboxypeptidase B (M81057) | 14 | 1.7 |
| TCCTCAAAA | No Match, See Table 2, P1 | 14 | 1.7 |
| AGCCTTGGT | Bile Salt Stimulated Lipase (X54457) | 12 | 1.4 |
| GTGTGCGCT | No Match | 11 | 1.3 |
| TGCGAGACC | No Match, See Table 2, P2 | 9 | 1.1 |
| GTGAAACCC | 21 Alu entries | 8 | 1.0 |
| GGTGACTCT | No Match | 8 | 1.0 |

TABLE 1-continued

Pancreatic SAGE Tags

| Tag | Gene | N | Percent |
|---|---|---|---|
| AAGGTAACA | Secretary Trypsin Inhibitor (M11949) | 6 | 0.7 |
| TCCCCTGTG | No Match | 5 | 0.6 |
| GTGACCACG | No Match | 5 | 0.6 |
| CCTGTAATC | M91159, M29366, 11 Alu entries | 5 | 0.6 |
| CACGTTGGA | No Match | 5 | 0.6 |
| AGCCCTACA | No Match | 5 | 0.6 |
| AGCACCTCC | Elongation Factor 2 (Z11692) | 5 | 0.6 |
| ACGCAGGGA | No Match, See Table 2, P3 | 5 | 0.6 |
| AATTGAAGA | No Match, See Table 2, P4 | 5 | 0.6 |
| TTCTGTGGG | No Match | 4 | 0.5 |
| TTCATACAC | No Match | 4 | 0.5 |
| GTGGCAGGC | NF-kB(X61499), Mu entry (S94541) | 4 | 0.5 |
| GTAAAACCC | TNF receptor 11 (M55994), Alu entry (X01448) | 4 | 0.5 |
| GAACACACA | No Match | 4 | 0.5 |
| CCTGGGAAG | Pancreatic Mucin (J05582) | 4 | 0.5 |
| CCCATCGTC (SEQ ID NO: 8–37) | Mitochondrial CytC Oxidase (X15759) | 4 | 0.5 |

SUMMARY

| | | | |
|---|---|---|---|
| SAGE tags occurring | Greater than three times | 380 | 45.2 |
| Occurring | Three times (15 × 3 =) | 45 | 5.4 |
| | Two times (32 × 2 =) | 64 | 7.6 |
| | One time | 351 | 41.8 |
| Total SAGE Tags | | 840 | 100.0 |

"Tag" indicates the 9 bp sequence unique to each tag, adjacent to the 4 bp anchoring NlaIII site. "N" and "Percent" indicates the number of times the tag was identified and its frequency, respectively. "Gene" indicates the accession number and description of GenBank R87 entries found to match the indicated tag using the SAGE software group with the following exceptions. When multiple entries were identified because of duplicated entries, only one entry is listed. In the cases of chymotrypsinogen, and trypsinogen 1, other genes were identified that were predicted to contain the same tags, but subsequent hybridization and sequence analysis identified the listed genes as the source of the tags. "Alu entry" indicates a match with a GenBank entry for a transcript that contained at least one copy of the alu consensus sequence (Deininger, et al., J Mol. Biol., 151:17, 1981).

Example 2

The quantitative nature of SAGE was evaluated by construction of an oligo-dT primed pancreatic cDNA library which was screened with cDNA probes for trypsinogen 1/2, procarboxpeptidase A1, chymotrypsinogen and elastase I-IIB/protease E. Pancreatic mRNA from the same preparation as used for SAGE in Example 1 was used to construct a cDNA library in the ZAP Express vector using the ZAP Express cDNA Synthesis kit following the manufacturer's protocol (Stratagene). Analysis of 15 randomly selected clones indicated that 100% contained cDNA inserts. Plates containing 250 to 500 plaques were hybridized as previously described (Ruppert, et al., Mol. Cell. Biol. 8:3104, 1988). cDNA probes for trypsinogen 1, trypsinogen 2, procarboxypeptidase A1, chymotrypsinogen, and elastase IIIB were derived by RT-PCR from pancreas RNA. The trypsinogen 1 and 2 probes were 93% identical and hybridized to the same plaques under the conditions used. Likewise, the elastase IIIB probe and protease E probe were over 95% identical and hybridized to the same plaques.

Figure 2:
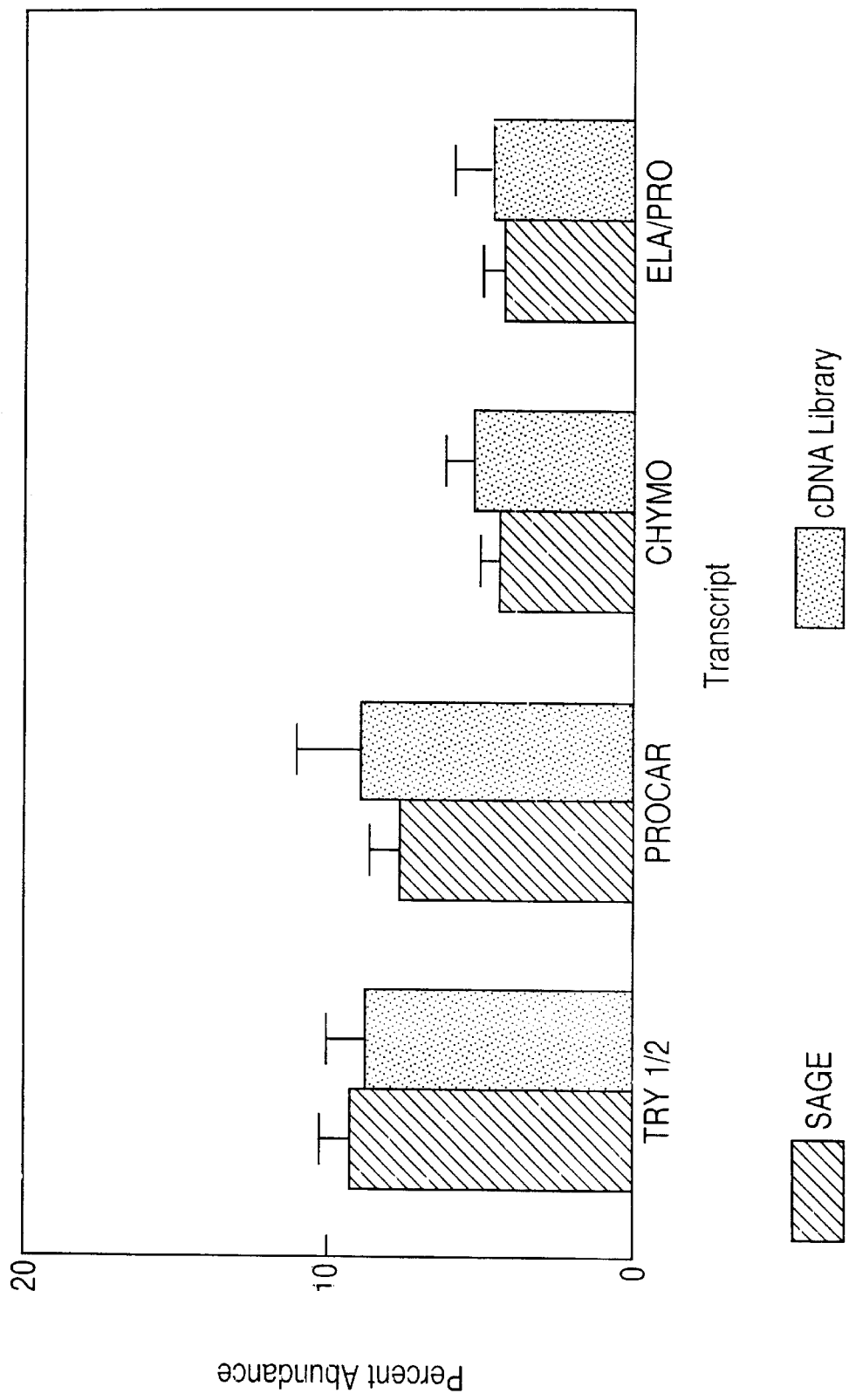
FIG. 2 shows a comparison of transcript abundance. Bars represent the percent abundance as determined by SAGE (dark bars) or hybridization analysis (light bars). SAGE quantitations were derived from Table 1 as follows: TRY 1/2 includes the tags for trypsinogen 1 and 2, PROCAR indicates tags for procarboxypeptidase A1, CHYMO indicates tags for chymotrypsinogen, and ELA/PRO includes the tags for elastase IIIB and protease E. Error bars represent the standard deviation determined by taking the square root of counted events and converting it to a percent abundance (assumed Poisson distribution).

The relative abundance of the SAGE tags for these transcripts was in excellent agreement with the results obtained with library screening (FIG. 2). Furthermore, whereas neither trypsinogen 1 and 2 nor elastase IIIB and protease E could be distinguished by the cDNA probes used to screen the library, all four transcripts could readily be distinguished on the basis of their SAGE tags (Table 1).

Example 3

Figure 3A:
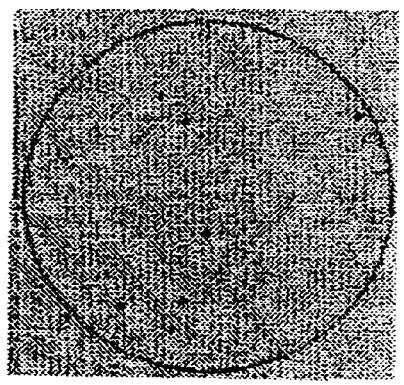
FIGS. 3A & 3B shows the results of screening a cDNA library with SAGE tags. P1 and P2 show typical hybridization results obtained with 13 bp oligonucleotides as described in the Examples. P1 and P2 correspond to the transcripts described in Table 2. Images were obtained using a Molecular Dynamics PhosphorImager and the circle indicates the outline of the filter membrane to which the recombinant phage were transferred prior to hybridization.
Figure 3B:
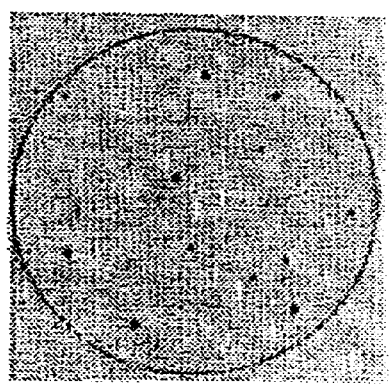

In addition to providing quantitative information on the abundance of known transcripts, SAGE could be used to identify novel expressed genes. While for the purposes of the SAGE analysis in this example, only the 9 bp sequence unique to each transcript was considered, each SAGE tag defined a 13 bp sequence composed of the anchoring enzyme (4 bp) site plus the 9 bp tag. To illustrate this potential, 13 bp oligonucleotides were used to isolate the transcripts corresponding to four unassigned tags (P1 to P4), that is, tags without corresponding entries from GenBank R87 (Table 1). In each of the four cases, it was possible to isolate multiple cDNA clones for the tag by simply screening the pancreatic cDNA library using 13 bp oligonucleotide as hybridization probe (examples in FIG. 3).

Plates containing 250 to 2,000 plaques were hybridized to oligonucleotide probes using the same conditions previously described for standard probes except that the hybridization temperature was reduced to room temperature. Washes were performed in 6.times.SSC/0.1% SDS for 30 minutes at room temperature. The probes consisted of 13 bp oligonucleotides which were labeled with $\gamma^2$P-ATP using T4 polynucleotide kinase. In each case, sequencing of the derived clones identified the correct SAGE tag at the predicted 3' end of the identified transcript. The abundance of plaques identified by hybridization with the 13-mers was in good agreement with that predicted by SAGE (Table 2). Tags P1 and P2 were found to correspond to amylase and preprocarboxypeptidase A2, respectively. No entry for preprocarboxypeptidase A2 and only a truncated entry for amylase was present in GenBank R87, thus accounting for their unassigned characterization. Tag P3 did not match any genes of known function in GenBank but did match numerous EST's, providing further evidence that it represented a bona fide transcript. The cDNA identified by P4 showed no significant homology, suggesting that it represented a previously uncharacterized pancreatic transcript.

TABLE 2

Characterization of Unassigned SAGE Tags

| Abundance TAG | SAGE SAGE | 13mer Hyb | Tag | Description |
|---|---|---|---|---|
| P1 TCCTCAAAA (6/388) | 1.7% (M28443) | 1.5% | + | 3' end of Pancreatic Amylase |
| P2 TGCGAGACC (43/3700) | 1.1% (U19977) | 1.2% | + | 3' end of Preprocarboxy-peptidase A2 |
| P3 ACGCAGGGA (5/2772) | 0.6% | 0.2% | + | EST match (R45808) |
| P4 AATTGAAGA (6/1587) | 0.6% | 0.4% | + | no match |

"Tag" and "SAGE Abundance" are described in Table 1; "13 mer Hyb" indicates the results obtained by screening a cDNA library with a 13 mer, as described above. The number of positive plaques divided by the total plaques screened is indicated in parentheses following the percent abundance. A positive in the "SAGE Tag" column indicates that the expected SAGE tag sequence was identified near the 3' end of isolated clones. "Description" indicates the results of BLAST searches of the daily updated GenBank entries at NCBI a of Jun. 9, 1995 (Altschul, et al., J Mol. Biol., 215:403, 1990). A description and Accession number are given for the most significant matches. P1 was found to match a truncated entry for amylase, and P2 was found to match an unpublished entry for preprocarboxypeptidase A2 which was entered after GenBank R87.

Example 4

Ditags produced by SAGE can be analyzed by PSA or CS, as described in the specification. In a preferred embodiment of PSA, the following steps are carried out with ditags: Ditags are prepared, amplified and cleaved with the anchoring enzyme as described in the previous examples.

OOOOOOOOOOXXXXXXXXXXCATG-3'

3'-GTACOOOOOOOOOOXXXXXXXXXX

Four-base oligomers containing an identifier (e.g., a fluorescent moiety, FL) are prepared that are complementary to the overhangs, for example, FL-CATG. The FL-CATG oligomers (in excess) are ligated to the ditags as shown below:

5'-FL-CATGOOOOOOOOOOXXXXXXXXXXCATG

GTACOOOOOOOOOOXXXXXXXXXXGTAC-FL-5'

The ditags are then purified and melted to yield single-stranded DNAs having the formula:

5'-FL-CATGOOOOOOOOOOXXXXXXXXXXCATG and

GTACOOOOOOOOOOXXXXXXXXXXGTAC-FL-5', for example. The mixture of single-stranded DNAs is preferably serially diluted. Each serial dilution is hybridized under appropriate stringency conditions with solid matrices containing gridded single-stranded oligonucleotides; all of the oligonucleotides contain a half-site of the anchoring enzyme cleavage sequence. In the example used herein, the oligonucleotide sequences contain a CATG sequence at the 5' end:

CATGOOOOOOOOOO, CATGXXXXXXXXXX, etc.

(or alternatively a CATG sequence at the 3' end: OOOOOOOOOOCATG)

The matrices can be constructed of any material known in the art and the oligonucleotide-bearing chips can be generated by any procedure known in the art, e.g. silicon chips containing oligonucleotides prepared by the VLSIP procedure (Fodor et al., supra).

The oligonucleotide-bearing matrices are evaluated for the presence or absence of a fluorescent ditag at each position in the grid.

In a preferred embodiment, there are $4^{10}$, or 1,048,576, oligonucleotides on the grid(s) of the general sequence CATGOOOOOOOOOO, such that every possible 10-base sequence is represented 3' to the CATG, where CATG is used as an example of an anchoring enzyme half site that is complementary to the anchoring enzyme half site at the 3' end of the ditag. Since there are estimated to be no more than 100,000 to 200,000 different expressed genes in the human genome, there are enough oligonucleotide sequences to detect all of the possible sequences adjacent to the 3'-most anchoring enzyme site observed in the cDNAs from the expressed genes in the human genome.

In yet another embodiment, structures as described above are amplified, cleaved with tagging enzyme and thereafter with anchoring enzyme to generate tag complements, which can then be labeled, melted, and hybridized with oligonucleotides on a solid support.

A determination is made of differential expression by comparing the fluorescence profile on the grids at different dilutions among different libraries (representing differential screening probes). For example:

| A | B | C | D | E |
|---|---|---|---|---|
| Library A, Ditags Diluted 1:10 | | | | |
| 1 | FL | | | |
| 2 | | | | FL |
| 3 | | FL | FL | |
| 4 | | | | FL |
| 5 | FL | | | |
| Library B, Ditags Diluted 1:10 | | | | |
| 1 | FL | | | |
| 2 | | | FL | FL |
| 3 | | FL | FL | |
| 4 | | | | |
| 5 | FL | | FL | |
| Library A, Ditags Diluted 1:50 | | | | |
| 1 | FL | | | |
| 2 | | | | |
| 3 | | FL | | |
| 4 | | | | FL |
| 5 | FL | | | |
| Library B, Ditags Diluted 1:5 | | | | |
| 1 | FL | | | |
| 2 | | | FL | |
| 3 | | FL | FL | |
| 4 | | | | |
| 5 | | | | |
| Library A, Ditags Diluted 1:100 | | | | |
| 1 | FL | | | |
| 2 | | | | |
| 3 | | FL | | |
| 4 | | | | FL |
| 5 | FL | | | |
| Library B, Ditags Diluted 1:100 | | | | |
| 1 | FL | | | |
| 2 | | | FL | |
| 3 | | FL | | |
| 4 | | | | |
| 5 | | | | |

The individual oligonucleotides thus hybridize to ditags with the following characteristics:

TABLE 3

| Dilution | 1:10 | | 1:50 | | 1:100 | |
|---|---|---|---|---|---|---|
| | Lib A | Lib B | Lib A | Lib B | Lib A | Lib B |
| 1A | + | + | + | + | + | + |
| 2C | | + | | + | | + |
| 2E | + | + | | | | |
| 3B | + | + | + | + | + | + |
| 3C | + | + | | + | | |

TABLE 3-continued

| Dilution | 1:10 | | 1:50 | | 1:100 | |
|---|---|---|---|---|---|---|
| | Lib A | Lib B | Lib A | Lib B | Lib A | Lib B |
| 4D | | | + | | + | + |
| 5A | + | + | + | | + | |
| 5E | | + | | | | |

Table 3 summarizes the results of the differential hybridization. Tags hybridizing to 1A and 3B reflect highly abundant nRNAs that are not differentially expressed (since the tags hybridize to both libraries at all dilutions); tag 2C identifies a highly abundant mRNA, but only in Library B. 2E reflects a low abundance transcript (since it is only detected at the lowest dilution) that is not found to be differentially expressed; 3C reflects a moderately abundant transcript (since it is expressed at the lower two dilutions) in Library B that is expressed at low abundance in Library A. 4D reflects a differentially-expressed, high abundance transcript restricted to Library A; 5A reflects a transcript that is expressed at high abundance in Library A but only at low abundance in Library B; and 5E reflects a differentially-expressed transcript that is detectable only in Library B.

In another PSA embodiment, step 3 above does not involve the use of a fluorescent or other identifier; instead, at the last round of amplification of the ditags, labeled dNTPs are used so that after melting, half of all molecules are labeled and can a serve as probes for hybridization to oligonucleotides fixed on the chips.

In yet another PSA embodiment, instead of ditags, a particular portion of the transcript is used, e.g., the sequence between the 3' terminus of the transcript and the first anchoring enzyme site. In that particular case, a double-stranded cDNA reverse transcript is generated as described in the Detailed Description. The transcripts are cut with the anchoring enzyme, a linker is added containing a PCR primer and amplification is initiated (using the primer at one end and the poly A tail at the other) while the transcripts are still on the strepavidin bead. At the last round of amplification, fluoresceinated dNTPs are used so that half of the molecules are labeled. The linker-primer can be optionally removed by use of the anchoring enzyme at this point in order to reduce the size of the fragments. The soluble fragments are then melted and captured on solid matrices containing CATGOOOOOOOOOO, as in the previous example. Analysis and scoring (only of the half of the fragments which contain fluoresceinated bases) is as described above.

For use in clonal sequencing, ditags or concatemers would be diluted and added to wells of multiwell plates, for example, or other receptacles so that on average the wells would contain, statistically, less than one DNA molecule per well (as is done in limited dilution for cell cloning). Each well would then receive reagents for PCR or another amplification process and the DNA in each receptacle would be sequenced, e.g., by mass spectroscopy. The results will either be a single sequence (there having been a single sequence in that receptacle), a "null" sequence (no DNA present) or a double sequence (more than one DNA molecule), which would be eliminated from consideration during data analysis. Thereafter, assessment of differential expression would be the same as described herein.

These results demonstrate that SAGE provides both quantitative and qualitative data about gene expression. The use of different anchoring enzymes and/or tagging enzymes with various recognition elements lends great flexibility to this strategy. In particular, since different anchoring enzymes cleave cDNA at different sites, the use of at least 2 different Aes on different samples of the same cDNA preparation allows confirmation of results and analysis of sequences that might not contain a recognition site for one of the enzymes.

Example 5

The Long SAGE method was performed using the standard SAGE protocol (available from sagent.org) with the following modifications. Linkers containing the MmeI recognition site were ligated to 3' cDNA ends after NlaIII digestion (Linker 1A 5'-TTTGGATTTGCTGGTGCAGT ACAACTAGGCTTAATATCCGACATG-3' (SEQ ID NO: 21) and Linker 1B 5'-TCGGATATTAAGCCTAGTTGTAC TGCACCAGCAAATCC Amino Modified C7-3' (SEQ ID NO: 22) were annealed together and ligated to half the cDNA population, and Linker 2A 5'-TTTCTGCTCG AATTCAAGCTTCTAACGATGTACGTCCGACATG-3' (SEQ ID NO: 23) and Linker 2B 5'-TCGGACGT ACATCGTTAGAAGCTTGAATTCGAGCAG Amino Modified C7-3' (SEQ ID NO: 24) were annealed together and ligated to the remaining half of the cDNA). Linker tag molecules were released from the cDNA using the MmeI type IIS restriction endonuclease. (University of Gdansk Center for Technology Transfer, Gdansk, Poland). Digestion was performed at 37° C. for 2.5 hrs using 40 U MmeI in 300 µL of 10 mM HEPES, pH 8.0, 2.5 mM KOAc, 5 mM MgOAc, 2 mM DTT, and 40 µM S-adenosylmethionine. To maximize the information content of the LSAGE tags the 2 bp 3' overhang created by digestion with MmeI was not polished, and the Linker 1 tag and Linker 2 tag molecules were ligated together in a 6 µl reaction containing 4 U T4 DNA ligase (GIBCO BRL) in the supplied buffer for 2.5 hours at 16° C. The SAGE software was modified to allow extraction of 21 bp tags from sequences of concatemer clones. A detailed protocol of the LSAGE method and the LSAGE software group is available at http://www.sagenet.org.

As efforts to fully characterize the genome near completion, SATE should allow a direct readout of expression in any given cell type or tissue. In the interim, a major application of SATE will be the comparison of gene expression patterns in among tissues and in various developmental and disease states in a given cell or tissue. One of skill in the art with the capability to perform PCR and manual sequencing could perform SAGE for this purpose. Adaptation of this technique to an automated sequencer would allow the analysis of over 1,000 transcripts in a single 3 hour run. An ABI 377 sequencer can produce a 451 bp readout for 36 templates in a 3 hour run (45 lbp/11 bp per tag.times.36=1476 tags). The appropriate number of tags to be determined will depend on the application. For example, the definition of genes expressed at relatively high levels (0.5% or more) in one tissue, but low in another, would require only a single day. Determination of transcripts expressed at greater than 100 mRNA's per cell (0.025% or more) should be quantifiable within a few months by a single investigator. Use of two different Anchoring Enzymes will ensure that virtually all transcripts of the desired abundance will be identified. The genes encoding those tags found to be most interesting on the basis of their differential representation can be positively identified by a combination of data-base searching, hybridization, and sequence analysis as demonstrated in Table 2. Obviously, SATE could also be applied to the analysis of organisms other than humans, and could direct investigation towards genes expressed in specific biologic states.

TABLE 4

Theoretical Matching of Tags to Genome.

| Tag length (N bp) | Complexity* $C = 4^{(N-4)}$ | Probability tag is unique in genome[+] $P(u) = [(C - 1)/C]^{30,000,000}$ |
|---|---|---|
| 14 | 1,048,576 | 0.00% |
| 15 | 4,194,304 | 0.08% |
| 16 | 16,777,216 | 16.73% |
| 17 | 67,108,864 | 63.95% |
| 18 | 268,435,456 | 89.43% |
| 19 | 1,073,741,824 | 97.24% |
| 20 | 4,294,967,296 | 99.30% |
| 21 | 17,179,869,184 | 99.83% |

*Complexity of tags is determined using a tag length comprised of a constant 4 bp sequence representing the restriction site at which the transcript was cleaved, followed by N bp derived from the adjacent sequence in each transcript.
[+]The probability that a tag is unique in the genome is determined assuming the genome contains ~30 × 10$^6$ NlaIII derived tags and is comprised of random sequence.

SATE, as described herein, allows comparison of expression of numerous genes among tissues or among different states of development of the same tissue, or between pathologic tissue and its normal counterpart. Such analysis is useful for identifying therapeutically, diagnostically and prognostically relevant genes, for example. Among the many utilities for SATE technology, is the identification of appropriate antisense or triple helix reagents which may be therapeutically useful. Further, gene therapy candidates can also be identified by the SATE technology. Other uses include diagnostic applications for identification of individual genes or groups of genes whose expression is shown to correlate to predisposition to disease, the presence of disease, and prognosis of disease, for example. An abundance profile, such as that depicted in Table 1, is useful for the above described applications. SATE is also useful for detection of an organism (e.g., a pathogen) in a host or detection of infection-specific genes expressed by a pathogen in a host.

The ability to identify a large number of expressed genes in a short period of time, as described by SATE in the present invention, provides unlimited uses. Although the invention has been described with reference to the presently preferred embodiment, it should be understood that various modifications can be made without departing from the spirit of the invention. Accordingly, the invention is limited only by the following claims.

What is claimed is:

1. In a method for detecting expressed transcripts in which a first defined nucleotide sequence tag is isolated from a first cDNA oligonucleotide and a second defined nucleotide sequence tag is isolated from a second cDNA oligonucleotide, and the first defined nucleotide sequence tag is linked to a first oligonucleotide linker thereby forming a first linked nucleic acid, wherein the first oligonucleotide linker comprises a recognition site for a restriction endonuclease that allows DNA cleavage at a site in the first defined nucleotide sequence tag distant from the first recognition site; and the second defined nucleotide sequence tag is linked to a second oligonucleotide linker thereby forming a second linked nucleic acid, wherein the second oligonucleotide linker comprises a second recognition site for the restriction endonuclease that allows DNA cleavage at a site in the first defined nucleotide sequence tag distant from the second recognition site; wherein the first and the second linked nucleic acids are cleaved with said restriction endonuclease; wherein the first and second tags are ligated to form ditags; and the nucleotide sequence of at least one tag of the ditag is determined to detect gene expression, the improvement comprising:

using MmeI as the restriction endonuclease to form 3' overhanging ends on said first and second tags.

2. A method for the detection of transcript expression comprising:

producing complementary deoxyribonucleic acid (cDNA) oligonucleotides;

isolating a first defined nucleotide sequence tag from a first cDNA oligonucleotide and a second defined nucleotide sequence tag from a second cDNA oligonucleotide;

linking the first tag to a first oligonucleotide linker thereby forming a first linked nucleic acid, wherein the first oligonucleotide linker comprises a first recognition site for MmeI restriction endonuclease;

linking the second tag to a second oligonucleotide linker thereby forming a second linked nucleic acid, wherein the second oligonucleotide linker comprises a second recognition site for MmeI restriction endonuclease;

cleaving the first and the second linked nucleic acids with MmeI restriction endonculease to form 3' overhanging ends;

ligating the first and second tags to form a ditag: and determining the nucleotide sequence of at least one tag of the ditag to detect transcript expression.

3. The method of claim 2 wherein the first oligonucleotide linker comprises a first amplification primer hybridization sequence, and the second oligonucleotide linker comprises a second amplification primer hybridization sequence; said method further comprising the step of amplifying the ditag oligonucleotide using primers which hybridize to the first and second amplification primer hybridization sequences.

4. The method of claim 2 further comprising producing concatemers of the ditags prior to the step of determining.

5. The method of claim 4 wherein the concatemer consists of about 2 to 200 ditags.

6. The method of claim 2 wherein said 3' overhanging ends are not removed to form blunt ends prior to said step of ligating.

7. The method of claim 2 wherein the first and second oligonucleotide linkers comprise the same nucleotide sequence.

8. The method of claim 2 wherein the first and second oligonucleotide linkers comprise different nucleotide sequences.

9. The method of claim 4 wherein the concatemer consists of about 8 to 20 ditags.

10. The method of claim 2 wherein the ditag is about 38 to 60 base pairs.

11. The method of claim 10 wherein the ditag is about 38 to 42 base pairs.

12. The method of claim 3 wherein the step of amplifying is performed by polymerase chain reaction (PCR).

13. The method of claim 2 further comprising the step of comparing the nucleotide sequence determined to a database comprising mammalian genomic sequences whereby matching sequences are identified.

14. A method for detection of transcript expression comprising:

cleaving a cDNA sample with a first restriction endonuclease, wherein the endonuclease cleaves the cDNA at a defined position in the cDNA thereby producing defined sequence tags;

isolating the defined cDNA tags and forming a pool of tags;

ligating the pool of tags with oligonucleotide linkers having a recognition site for a second restriction endonuclease which is MmeI which forms 3' overhanging ends;

cleaving the tags with MmeI restriction endonuclease to form 3' overhanging ends;

ligating the pool of tags to produce at least one ditag; and determining the nucleotide sequence of at least one ditag, wherein the nucleotide sequence of the ditag corresponds to sequence from at least one expressed transcripts.

15. The method of claim 14 further comprising amplifying the at least one ditag.

16. The method of claim 14 wherein the 3' overhanging ends are not removed to form blunt ends prior to said step of ligating.

17. The method of claim 14 wherein the first restriction endonuclease has a four base pair recognition site.

18. The method of claim 17 wherein the first restriction endonuclease is NlaIII.

19. The method of claim 14 wherein the cDNA comprises a means for capture.

20. The method of claim 19 wherein the means for capture is a binding element.

21. The method of claim 20 wherein the binding element is biotin.

22. The method of claim 14 wherein the oligonucleotide linkers comprise a homogeneous population having a single nucleotide sequence.

23. The method of claim 14 wherein the oligonucleotide linkers comprise a first and second linker each having a distinct nucleotide sequence.

24. The method of claim 14 wherein said 3' overhanging ends are removed to form blunt ends prior to said step of ligating.

25. The method of claim 14 wherein the ditag is about 38 to 60 base pairs.

26. The method of claim 14 further comprising ligating the ditags to produce a concatemer.

27. The method of claim 26 wherein the concatemer consists of about 2 to 200 ditags.

28. The method of claim 27 wherein the concatemer consists of about 8 to 20 ditags.

29. The method of claim 15 wherein the amplifying is by polymerase chain reaction (PCR).

30. The method of claim 14 wherein the oligonucleotide linkers comprise an amplification primer hybridization sequence.

* * * * *

SEQUENCE LISTING

<160> NUMBER OF SEQ ID NOS: 30

<210> SEQ ID NO 1

```
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 1
atcacgccct                                                            10

<210> SEQ ID NO 2
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 2
atcacgccct cataatc                                                    17

<210> SEQ ID NO 3
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 3
tcacccaggg                                                            10

<210> SEQ ID NO 4
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 4
tcacccaggg acccatt                                                    17

<210> SEQ ID NO 5
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 5
ttggtgatac                                                            10

<210> SEQ ID NO 6
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 6
ttggtgatac cccccgg                                                    17

<210> SEQ ID NO 7
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 7
```

```
aaacaaatca                                                          10
```

<210> SEQ ID NO 8
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 8

```
aaacaaatca ccatcct                                                  17
```

<210> SEQ ID NO 9
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 9

```
ccgtggtagc                                                          10
```

<210> SEQ ID NO 10
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 10

```
ccgtggtagc caatgtt                                                  17
```

<210> SEQ ID NO 11
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 11

```
gaaggagatg                                                          10
```

<210> SEQ ID NO 12
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 12

```
gaaggagatg gcgaaag                                                  17
```

<210> SEQ ID NO 13
<211> LENGTH: 9
<212> TYPE: DNA
<213> ORGANISM: Artificial Sequence
<220> FEATURE:
<223> OTHER INFORMATION: tag or tag concatamer

<400> SEQUENCE: 13

```
gccgctctc                                                            9
```

<210> SEQ ID NO 14
<211> LENGTH: 16
<212> TYPE: DNA

```
<213> ORGANISM: Artificial Sequence
<220> FEATURE:
<223> OTHER INFORMATION: tag or tag concatamer

<400> SEQUENCE: 14
gccgctctcc cggacc                                                    16

<210> SEQ ID NO 15
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 15
tcttaccata                                                           10

<210> SEQ ID NO 16
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 16
tcttaccata cacactg                                                   17

<210> SEQ ID NO 17
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 17
tggataattc                                                           10

<210> SEQ ID NO 18
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 18
tggataattc aaacaaa                                                   17

<210> SEQ ID NO 19
<211> LENGTH: 10
<212> TYPE: DNA
<213> ORGANISM: Artificial Sequence
<220> FEATURE:
<223> OTHER INFORMATION: tag or tag concatamer

<400> SEQUENCE: 19
ttccagccaa                                                           10

<210> SEQ ID NO 20
<211> LENGTH: 17
<212> TYPE: DNA
<213> ORGANISM: Artificial Sequence
<220> FEATURE:
<223> OTHER INFORMATION: tag or tag concatamer

<400> SEQUENCE: 20
ttccagccaa tggatga                                                   17
```

<210> SEQ ID NO 21
<211> LENGTH: 45
<212> TYPE: DNA
<213> ORGANISM: Artificial Sequence
<220> FEATURE:
<223> OTHER INFORMATION: linker

<400> SEQUENCE: 21
tttggatttg ctggtgcagt acaactaggc ttaatatccg acatg                45

<210> SEQ ID NO 22
<211> LENGTH: 38
<212> TYPE: DNA
<213> ORGANISM: Artificial Sequence
<220> FEATURE:
<223> OTHER INFORMATION: linker
<221> NAME/KEY: modified_base
<222> LOCATION: 38
<223> OTHER INFORMATION: amino modifid C7

<400> SEQUENCE: 22
tcggatatta agcctagttg tactgcacca gcaaatcc                        38

<210> SEQ ID NO 23
<211> LENGTH: 43
<212> TYPE: DNA
<213> ORGANISM: Artificial Sequence
<220> FEATURE:
<223> OTHER INFORMATION: linker

<400> SEQUENCE: 23
tttctgctcg aattcaagct tctaacgatg tacgtccgac atg                  43

<210> SEQ ID NO 24
<211> LENGTH: 36
<212> TYPE: DNA
<213> ORGANISM: Artificial Sequence
<220> FEATURE:
<223> OTHER INFORMATION: linker
<221> NAME/KEY: modified_base
<222> LOCATION: 36
<223> OTHER INFORMATION: amino modified C7

<400> SEQUENCE: 24
tcggacgtac atcgttagaa gcttgaattc gagcag                          36

<210> SEQ ID NO 25
<211> LENGTH: 18
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(18)
<223> OTHER INFORMATION: n = A,T,C or G

<400> SEQUENCE: 25
ggatgcatgn nnnnnnnn                                              18

<210> SEQ ID NO 26
<211> LENGTH: 36
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(36)

-continued

```
<223> OTHER INFORMATION: n = A,T,C or G

<400> SEQUENCE: 26
ggatgcatgn nnnnnnnnn nnnnnnncat gcatcc                              36

<210> SEQ ID NO 27
<211> LENGTH: 48
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(48)
<223> OTHER INFORMATION: n = A,T,C or G

<400> SEQUENCE: 27 catgnnnnn nnnnnnnnn nncatgnnnn nnnnnnnnnn nnnncatg                  48

<210> SEQ ID NO 28
<211> LENGTH: 26
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(26)
<223> OTHER INFORMATION: n = A,T,C or G

<400> SEQUENCE: 28
tccracatgn nnnnnnnnn nnnnnn                                         26

<210> SEQ ID NO 29
<211> LENGTH: 52
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(52)
<223> OTHER INFORMATION: n = A,T,C or G

<400> SEQUENCE: 29
tccracatgn nnnnnnnnn nnnnnnnnn nnnnnnnnn nnncatgtyc ca              52

<210> SEQ ID NO 30
<211> LENGTH: 80
<212> TYPE: DNA
<213> ORGANISM: Artificial Sequence
<220> FEATURE:
<223> OTHER INFORMATION: tag or tag concatamer
<221> NAME/KEY: misc_feature
<222> LOCATION: (1)...(80)
<223> OTHER INFORMATION: n = A,T,C or G

<400> SEQUENCE: 30 catgnnnnn nnnnnnnnn nnnnnnnnn nnnnnnnca tgnnnnnnnn nnnnnnnnn        60 nnnnnnnnn nnnnnncatg                                                80
```